(12) United States Patent
Conklin

(10) Patent No.: US 9,345,574 B2
(45) Date of Patent: May 24, 2016

(54) FORCE-BASED HEART VALVE SIZER

(71) Applicant: Edwards Lifesciences Corporation, Irvine, CA (US)

(72) Inventor: Brian S. Conklin, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 609 days.

(21) Appl. No.: 13/707,395

(22) Filed: Dec. 6, 2012

(65) Prior Publication Data
US 2013/0150954 A1 Jun. 13, 2013

Related U.S. Application Data

(60) Provisional application No. 61/568,913, filed on Dec. 9, 2011.

(51) Int. Cl.
*A61F 2/24* (2006.01)
*A61B 5/107* (2006.01)
*A61B 19/00* (2006.01)

(52) U.S. Cl.
CPC .............. *A61F 2/2496* (2013.01); *A61B 5/1076* (2013.01); *A61B 2019/464* (2013.01); *A61B 2019/465* (2013.01); *A61B 2019/466* (2013.01); *A61F 2/243* (2013.01); *A61F 2250/0073* (2013.01)

(58) Field of Classification Search
CPC ..... A61F 2/2496; A61F 2/243; A61B 5/1076; A61B 2019/464; A61B 2019/465; A61B 2019/466
See application file for complete search history.

(56) References Cited

U.S. PATENT DOCUMENTS

| 528,759 A | 11/1894 | Bernhardt |
|---|---|---|
| 3,164,009 A | 1/1965 | Schaschl |
| 4,016,867 A | 4/1977 | King et al. |

(Continued)

FOREIGN PATENT DOCUMENTS

| EP | 2080474 A1 | 7/2009 |
|---|---|---|
| GB | 2083362 A | 3/1982 |

(Continued)

OTHER PUBLICATIONS

"Torque limiter". Wikipedia, The Free Encyclopedia. https://en.wikipedia.org/w/index.php?title=Torque_limiter&oldid=443865421. Revised Aug. 9, 2011.*

(Continued)

*Primary Examiner* — Devin Henson
(74) *Attorney, Agent, or Firm* — AnneMarie Kaiser; Guy Cumberbatch; Pui Tong Ho

(57) ABSTRACT

A valve sizer for determining an appropriate replacement valve size when performing a heart valve replacement procedure is provided. In one version the valve sizer has a hollow shaft with proximal and distal ends. A movable sizing element couples to the distal end of the shaft and is radially expandable between first, contracted and second, expanded positions. An actuator assembly on a handle includes an actuator coupled to a clutch member via a ball-spring-detent clutch. A rod extends through the shaft and maintains a fixed distance between the handle and a distal hub in the sizing element. Movement of the actuator causes axial movement of the shaft, thereby causing radial expansion of sizing petals relative to the hub. The clutch slips when a predetermined reaction force from the surrounding valve annulus is met by the petals.

17 Claims, 25 Drawing Sheets

(56) References Cited

U.S. PATENT DOCUMENTS

| | | | |
|---|---|---|---|
| 4,185,638 A | 1/1980 | Bruner | |
| 4,211,241 A | 7/1980 | Kaster et al. | |
| 4,362,167 A | 12/1982 | Nicolai et al. | |
| 4,566,465 A | 1/1986 | Arhan et al. | |
| 4,643,194 A | 2/1987 | Fogarty | |
| 4,940,459 A | 7/1990 | Noce | |
| 5,010,892 A | 4/1991 | Colvin et al. | |
| 5,042,161 A | 8/1991 | Hodge | |
| 5,360,014 A | 11/1994 | Sauter et al. | |
| 5,489,296 A | 2/1996 | Love et al. | |
| 5,531,785 A | 7/1996 | Love et al. | |
| 5,545,214 A | 8/1996 | Stevens | |
| 5,573,007 A | 11/1996 | Bobo, Sr. | |
| 5,716,417 A | 2/1998 | Girard et al. | |
| 5,728,064 A | 3/1998 | Burns et al. | |
| 5,752,522 A | 5/1998 | Murphy | |
| 5,814,098 A * | 9/1998 | Hinnenkamp | A61F 2/2496 33/512 |
| 5,848,969 A | 12/1998 | Panescu et al. | |
| 5,855,563 A | 1/1999 | Kaplan et al. | |
| 5,865,801 A | 2/1999 | Houser | |
| 5,885,228 A | 3/1999 | Rosenman et al. | |
| 5,919,147 A | 7/1999 | Jain | |
| 5,921,934 A | 7/1999 | Teo | |
| 5,921,935 A | 7/1999 | Hickey | |
| 6,010,511 A | 1/2000 | Murphy | |
| 6,019,739 A | 2/2000 | Rhee et al. | |
| 6,042,554 A | 3/2000 | Rosenman et al. | |
| 6,045,576 A | 4/2000 | Starr et al. | |
| 6,050,973 A | 4/2000 | Duffy | |
| 6,081,737 A | 6/2000 | Shah | |
| 6,083,179 A | 7/2000 | Oredsson | |
| 6,099,475 A | 8/2000 | Seward et al. | |
| 6,110,200 A | 8/2000 | Hinnenkamp | |
| 6,136,017 A | 10/2000 | Craver et al. | |
| 6,210,338 B1 | 4/2001 | Afremov et al. | |
| 6,319,281 B1 | 11/2001 | Patel | |
| 6,322,526 B1 | 11/2001 | Rosenman et al. | |
| 6,350,281 B1 | 2/2002 | Rhee | |
| 6,582,419 B1 | 6/2003 | Schoon et al. | |
| 6,598,307 B2 | 7/2003 | Love et al. | |
| 6,730,021 B2 * | 5/2004 | Vassiliades, Jr. | A61B 17/0206 600/202 |
| 6,942,694 B2 | 9/2005 | Liddicoat et al. | |
| 7,007,396 B2 | 3/2006 | Rudko et al. | |
| 7,258,698 B2 | 8/2007 | Lemmon | |
| 7,270,142 B2 | 9/2007 | Acosta | |
| 7,637,943 B2 | 12/2009 | Lemmon | |
| 7,713,216 B2 | 5/2010 | Dubey et al. | |
| 7,842,084 B2 | 11/2010 | Bicer | |
| 8,057,396 B2 | 11/2011 | Forster et al. | |
| 8,449,625 B2 | 5/2013 | Campbell et al. | |
| 8,475,521 B2 | 7/2013 | Suri et al. | |
| 2002/0020074 A1 | 2/2002 | Love et al. | |
| 2004/0237321 A1 | 12/2004 | Rudko et al. | |
| 2006/0144441 A1 | 7/2006 | Acosta | |
| 2006/0195134 A1 | 8/2006 | Crittenden | |
| 2006/0287718 A1 | 12/2006 | Bicer | |
| 2007/0299513 A1 | 12/2007 | Ryan et al. | |
| 2008/0033544 A1 | 2/2008 | Lemmon | |
| 2009/0093877 A1 | 4/2009 | Keidar et al. | |
| 2009/0132036 A1 | 5/2009 | Navia | |
| 2009/0182419 A1 | 7/2009 | Bolling | |
| 2009/0192600 A1 | 7/2009 | Ryan | |
| 2009/0192602 A1 | 7/2009 | Kuehn | |
| 2009/0192603 A1 | 7/2009 | Ryan | |
| 2009/0192604 A1 | 7/2009 | Gloss | |
| 2010/0152844 A1 | 6/2010 | Couetil | |
| 2010/0249661 A1 * | 9/2010 | Righini | A61B 5/103 600/587 |
| 2011/0098602 A1 * | 4/2011 | Campbell | A61B 5/1076 600/587 |
| 2011/0295107 A1 * | 12/2011 | Kargar | A61B 5/1076 600/424 |
| 2013/0103064 A1 * | 4/2013 | Arenson et al. | 606/169 |

FOREIGN PATENT DOCUMENTS

| | | |
|---|---|---|
| GB | 2137499 A | 10/1984 |
| WO | 9640006 A1 | 12/1996 |
| WO | 9725003 A1 | 7/1997 |
| WO | 9741801 A1 | 11/1997 |
| WO | 9742871 A1 | 11/1997 |
| WO | 2010090720 A1 | 8/2010 |
| WO | 2010111621 A1 | 9/2010 |
| WO | 2011106354 A1 | 9/2011 |

OTHER PUBLICATIONS

International Search Report from corresponding international application No. PCT/US2012/068443 dated Mar. 25, 2013.

* cited by examiner

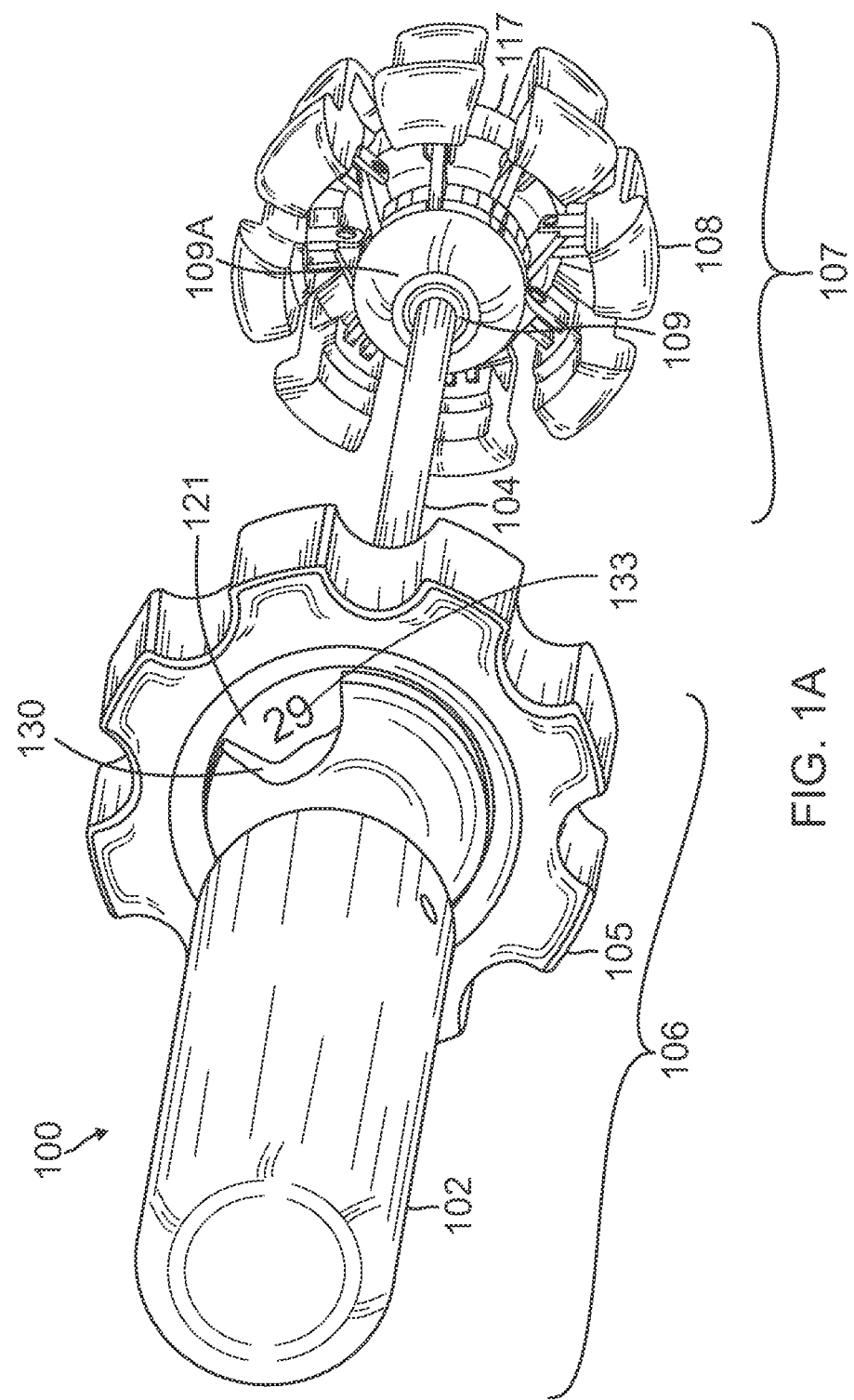

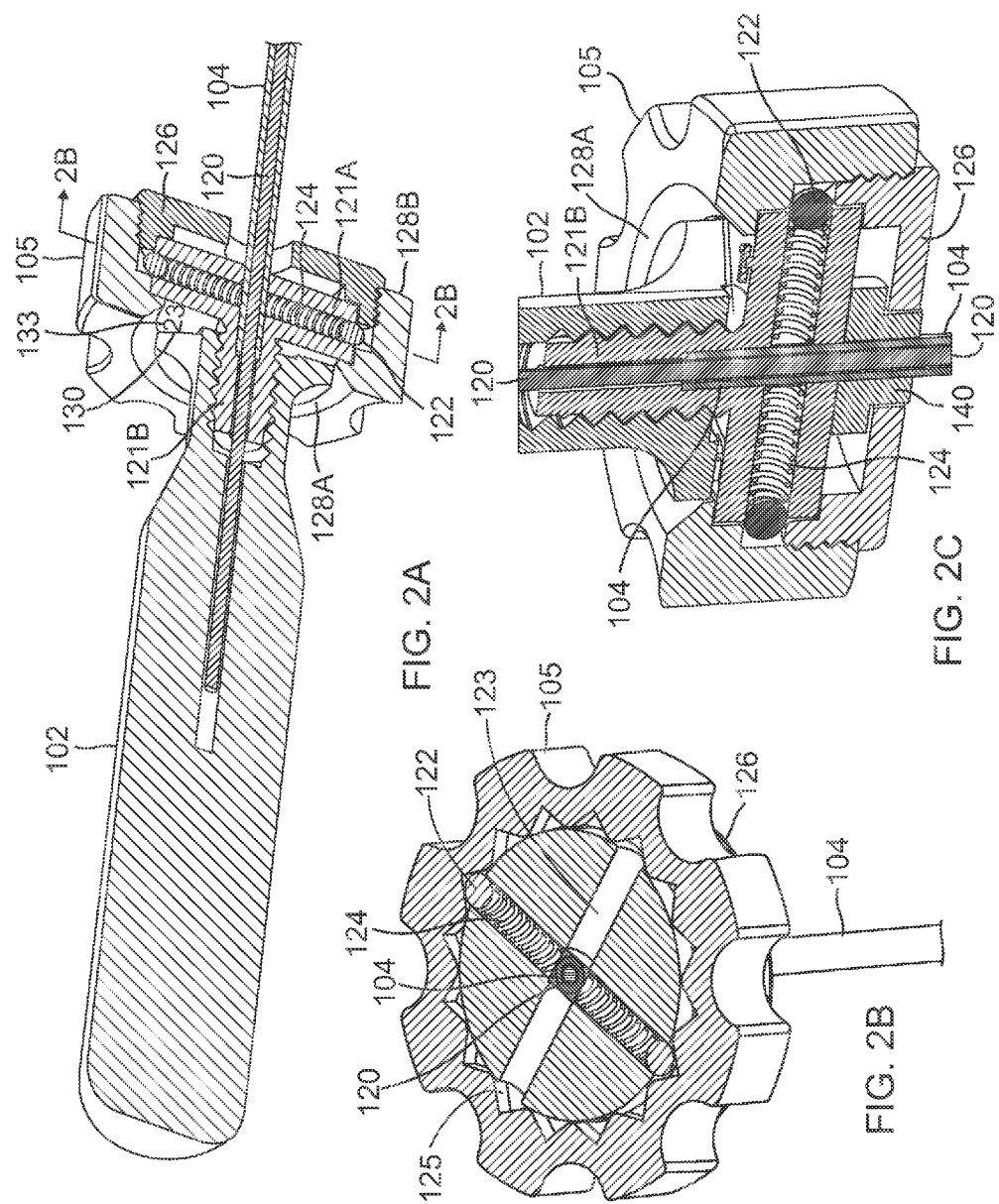

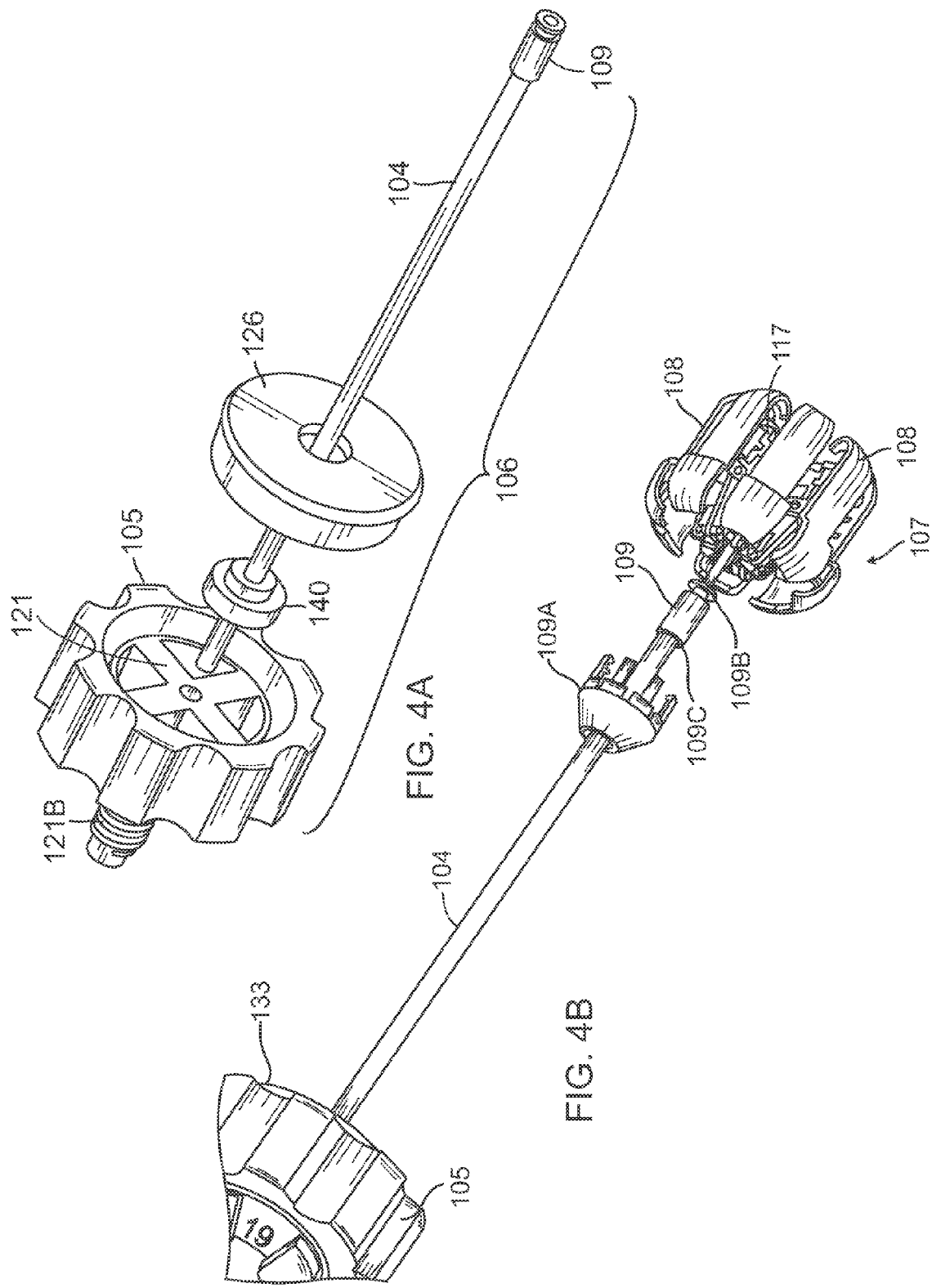

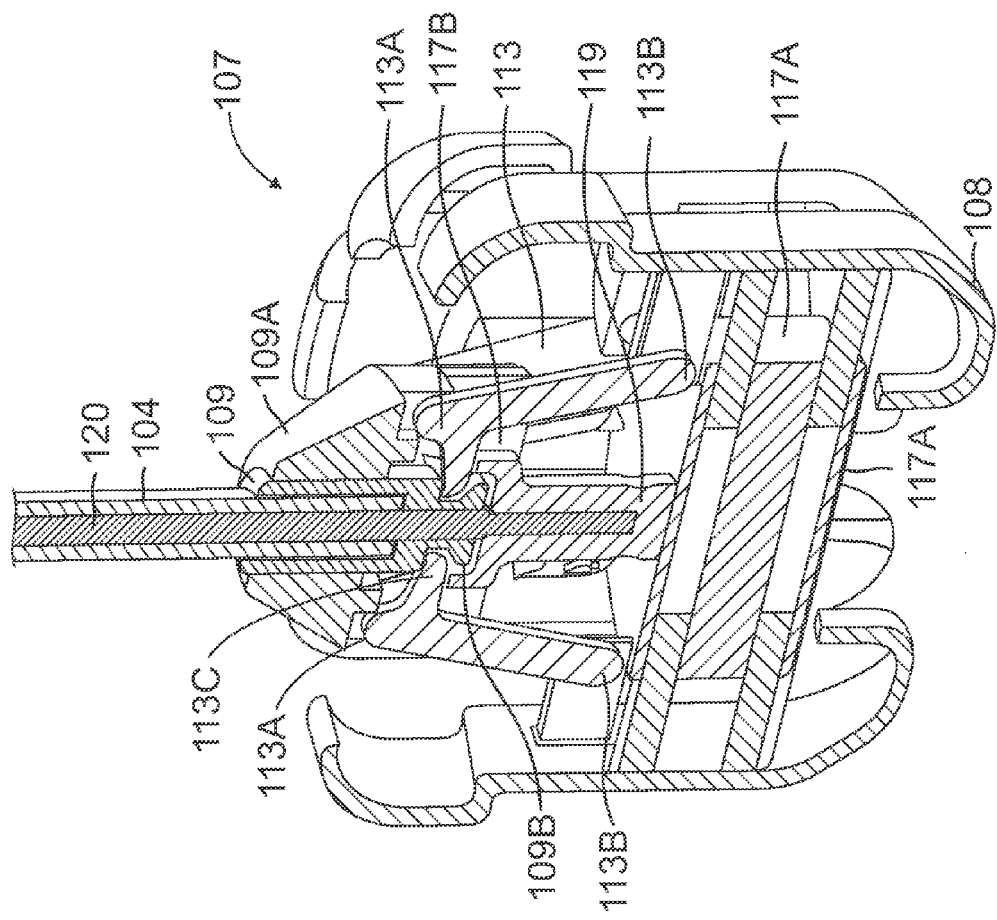
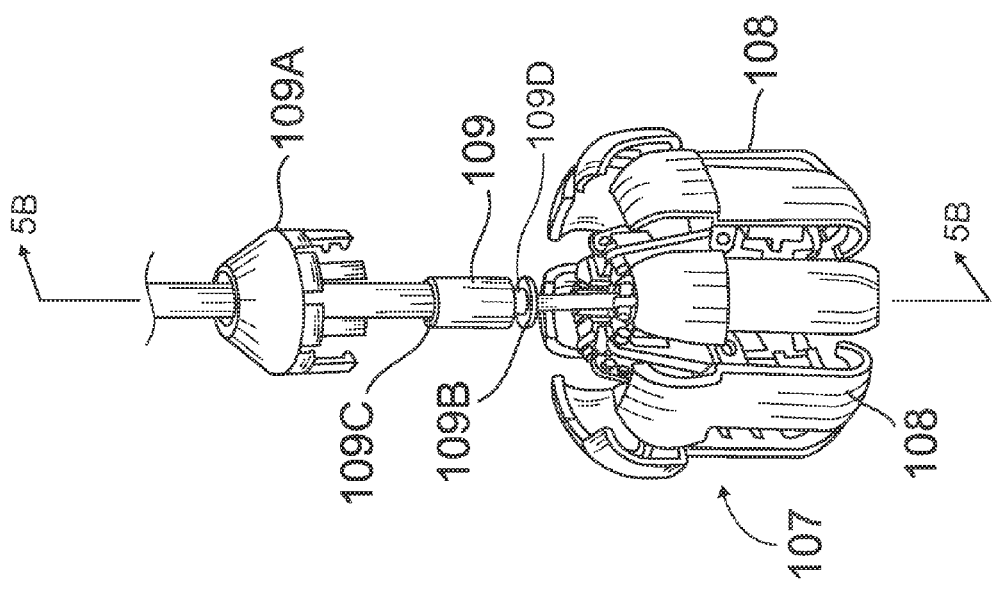

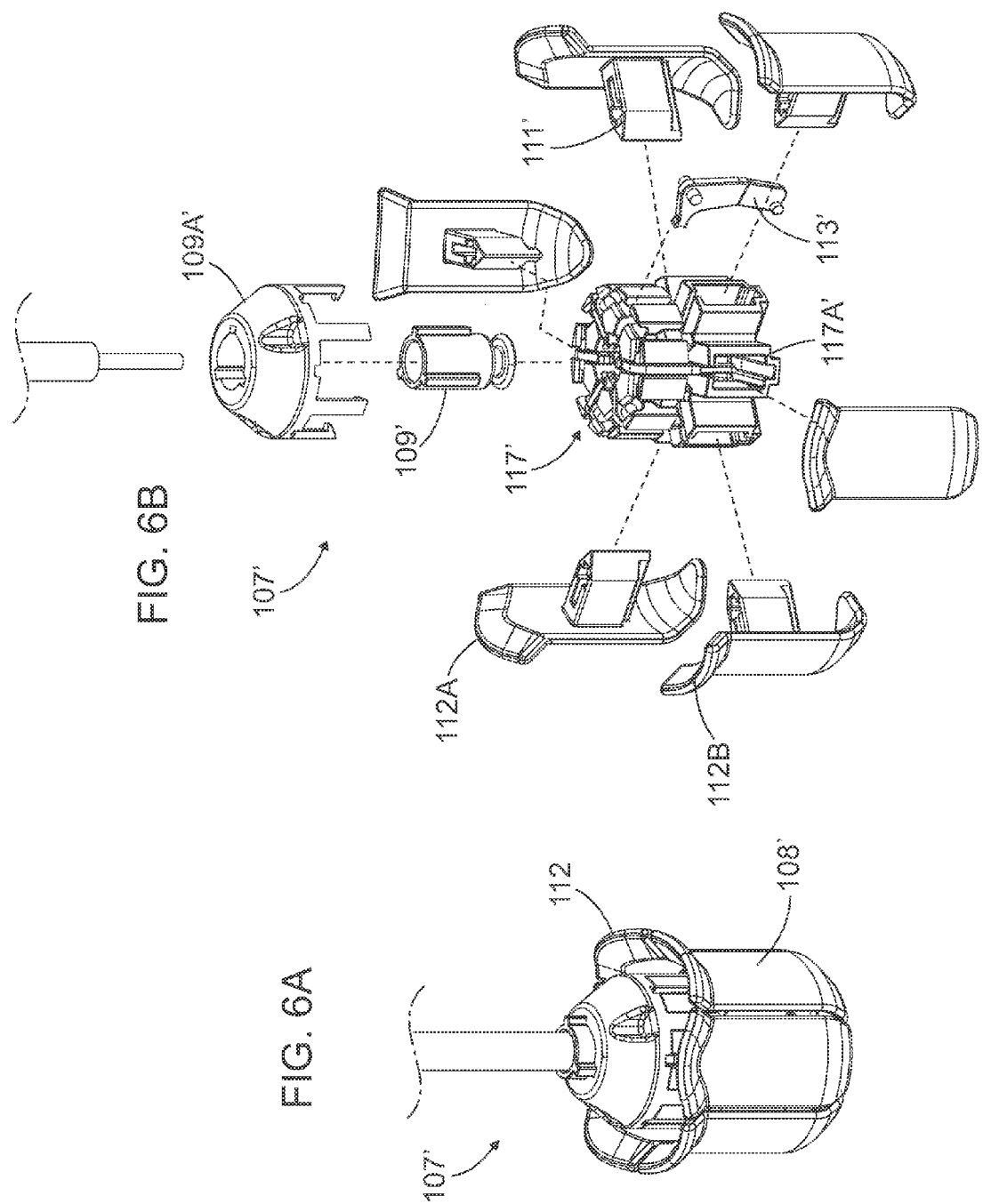

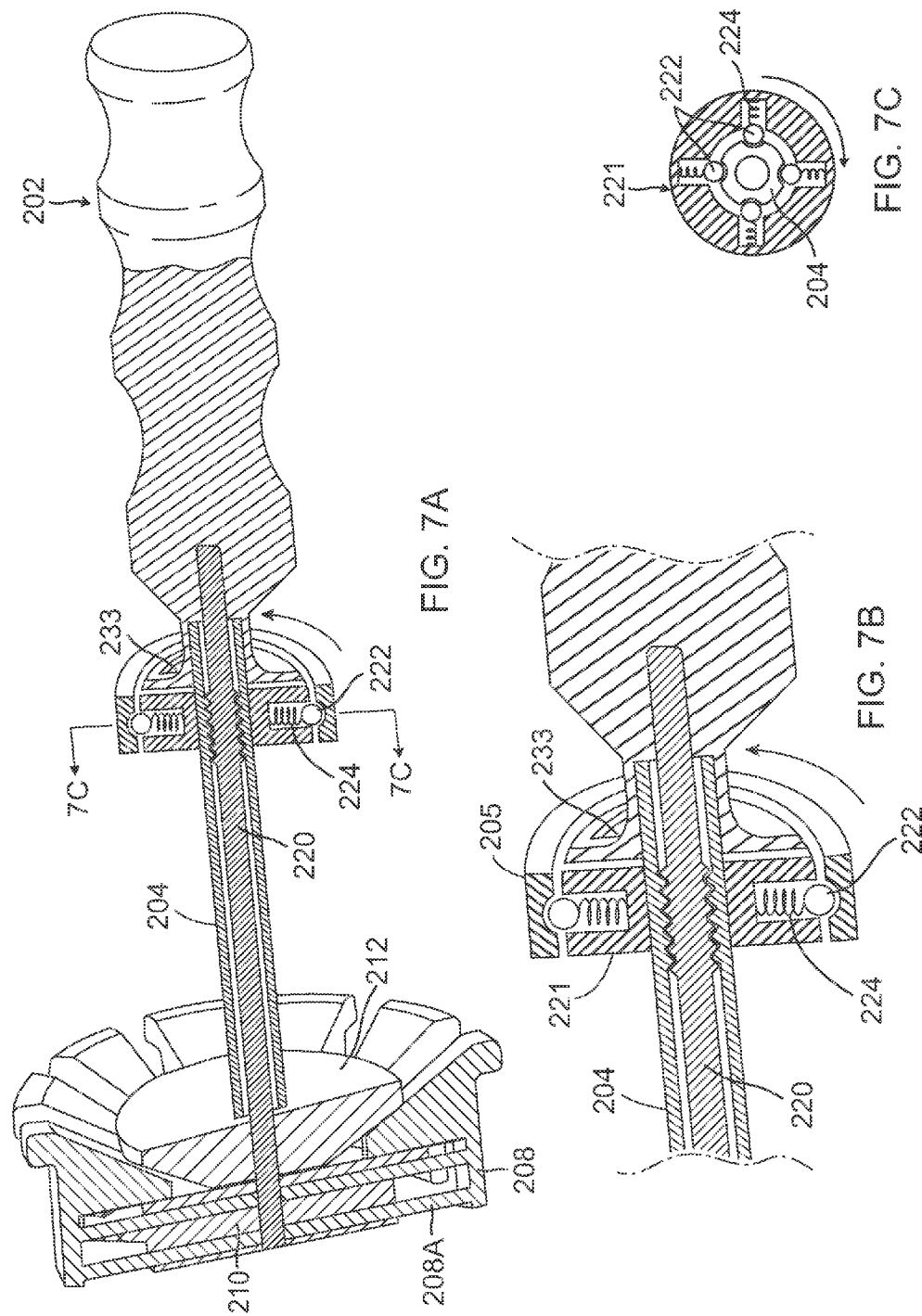

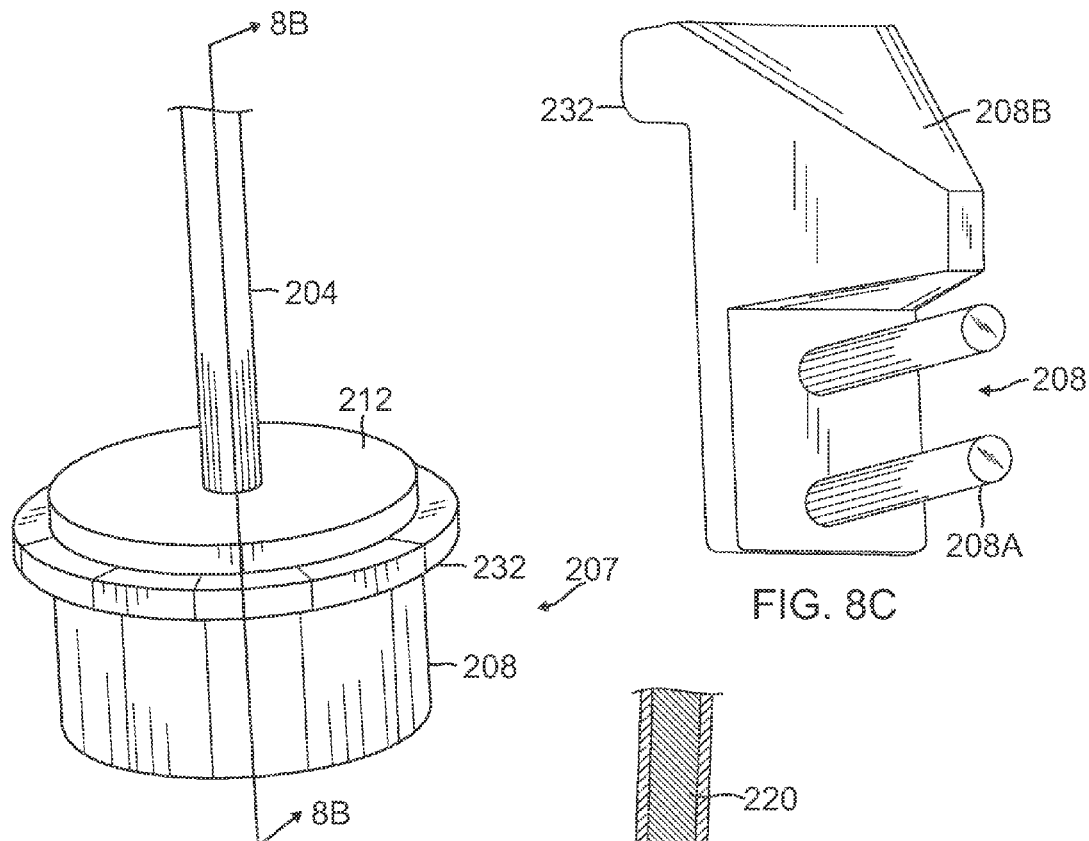
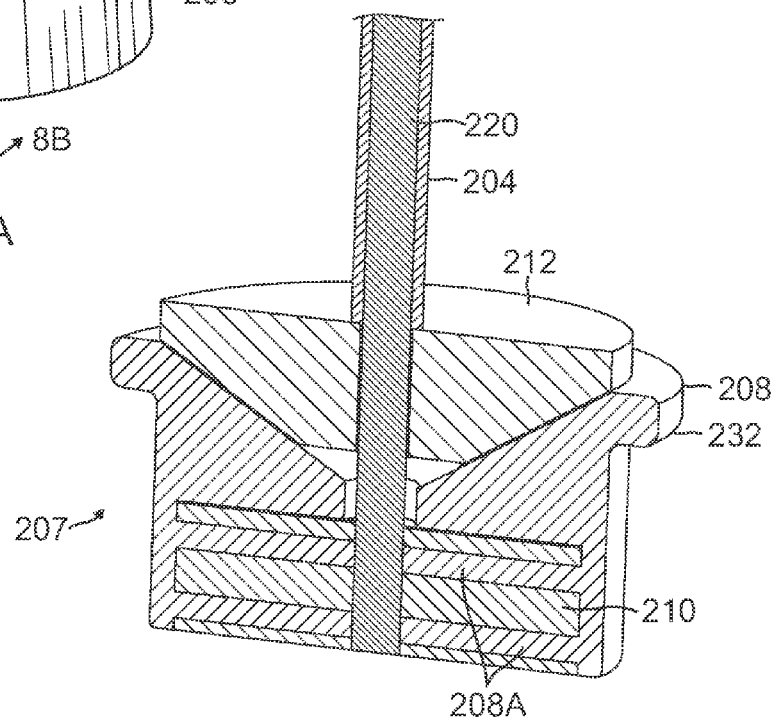

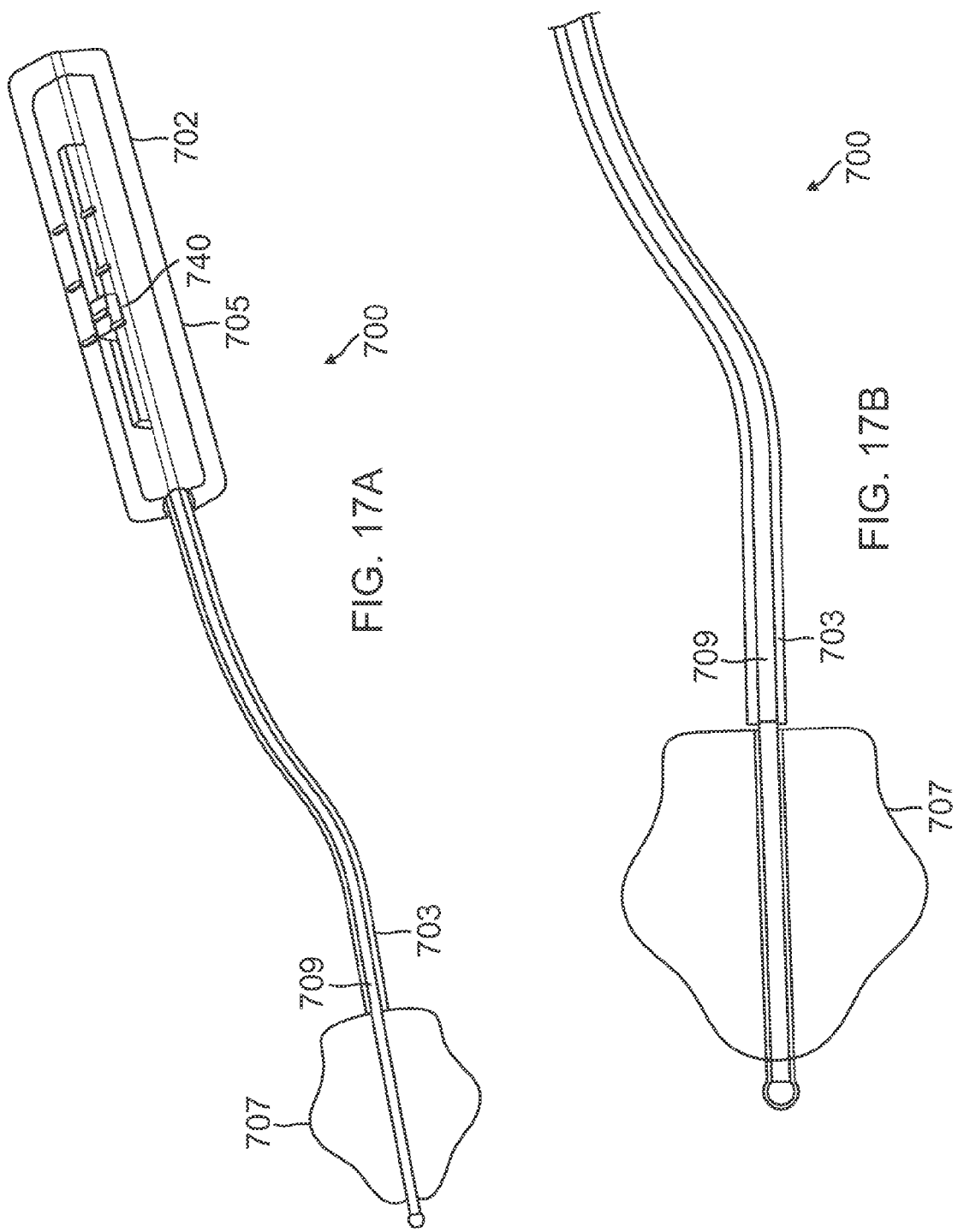

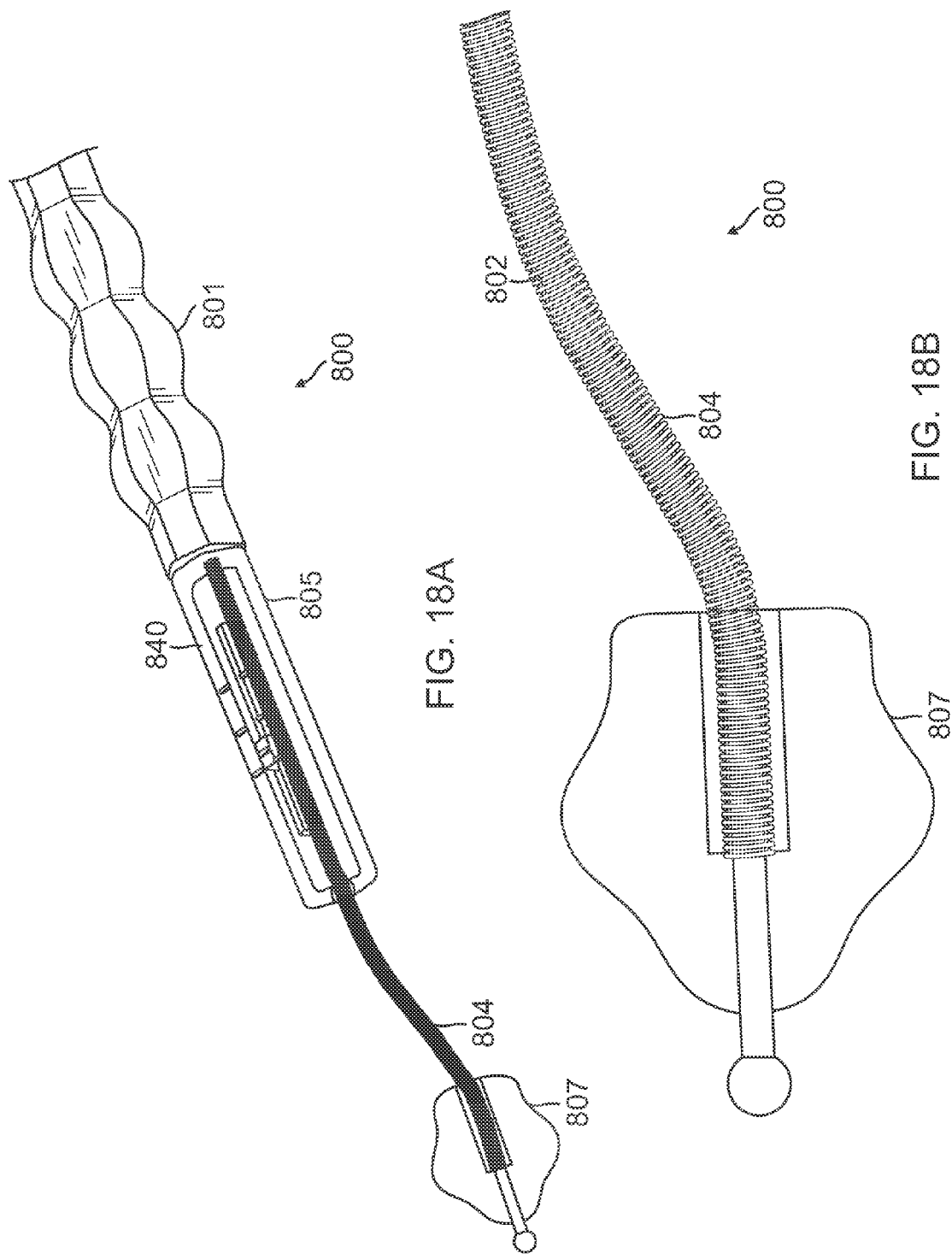

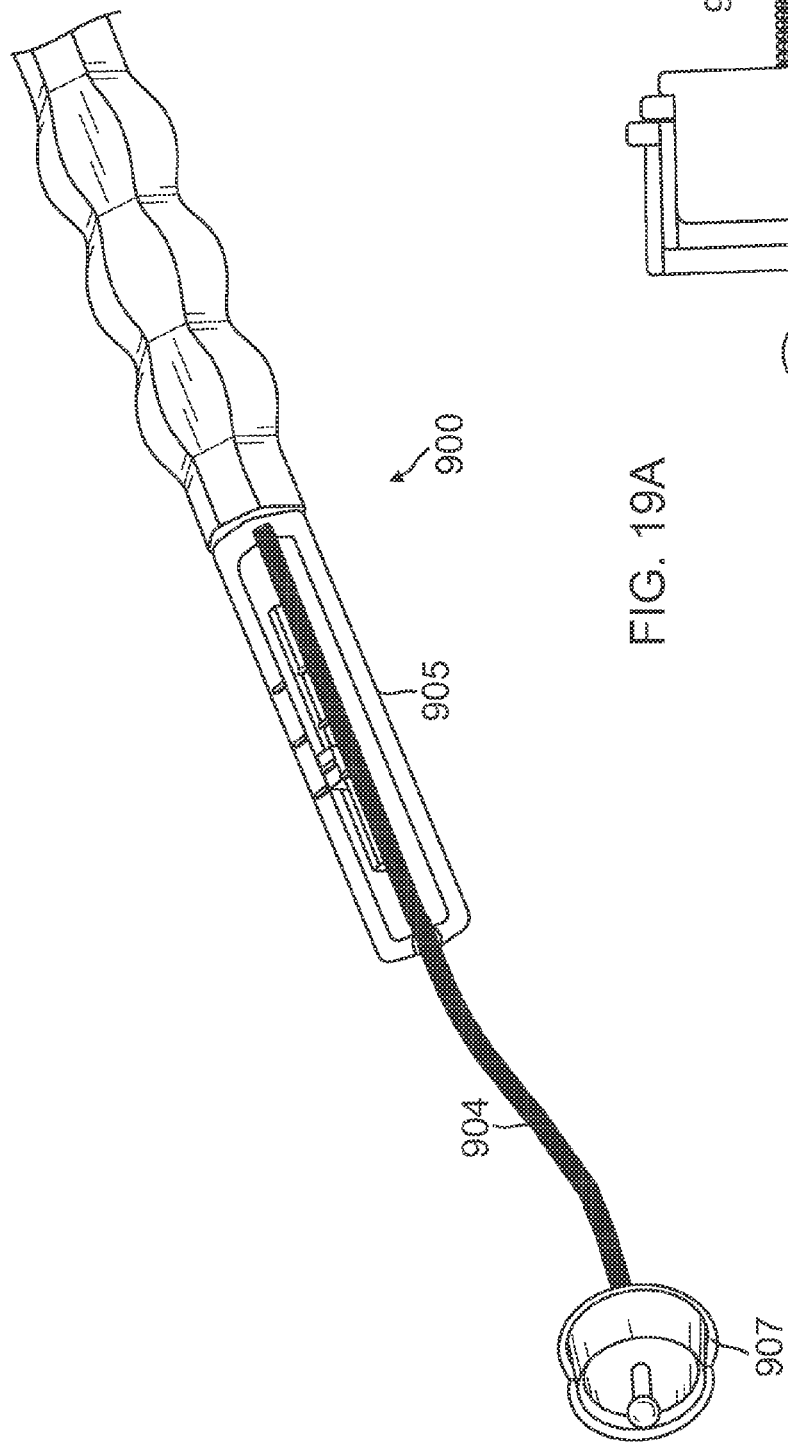
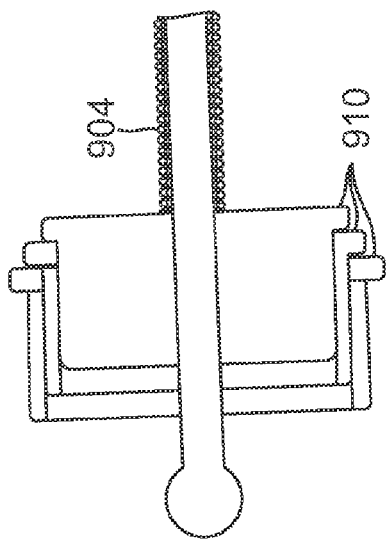
FIG. 19A
FIG. 19B

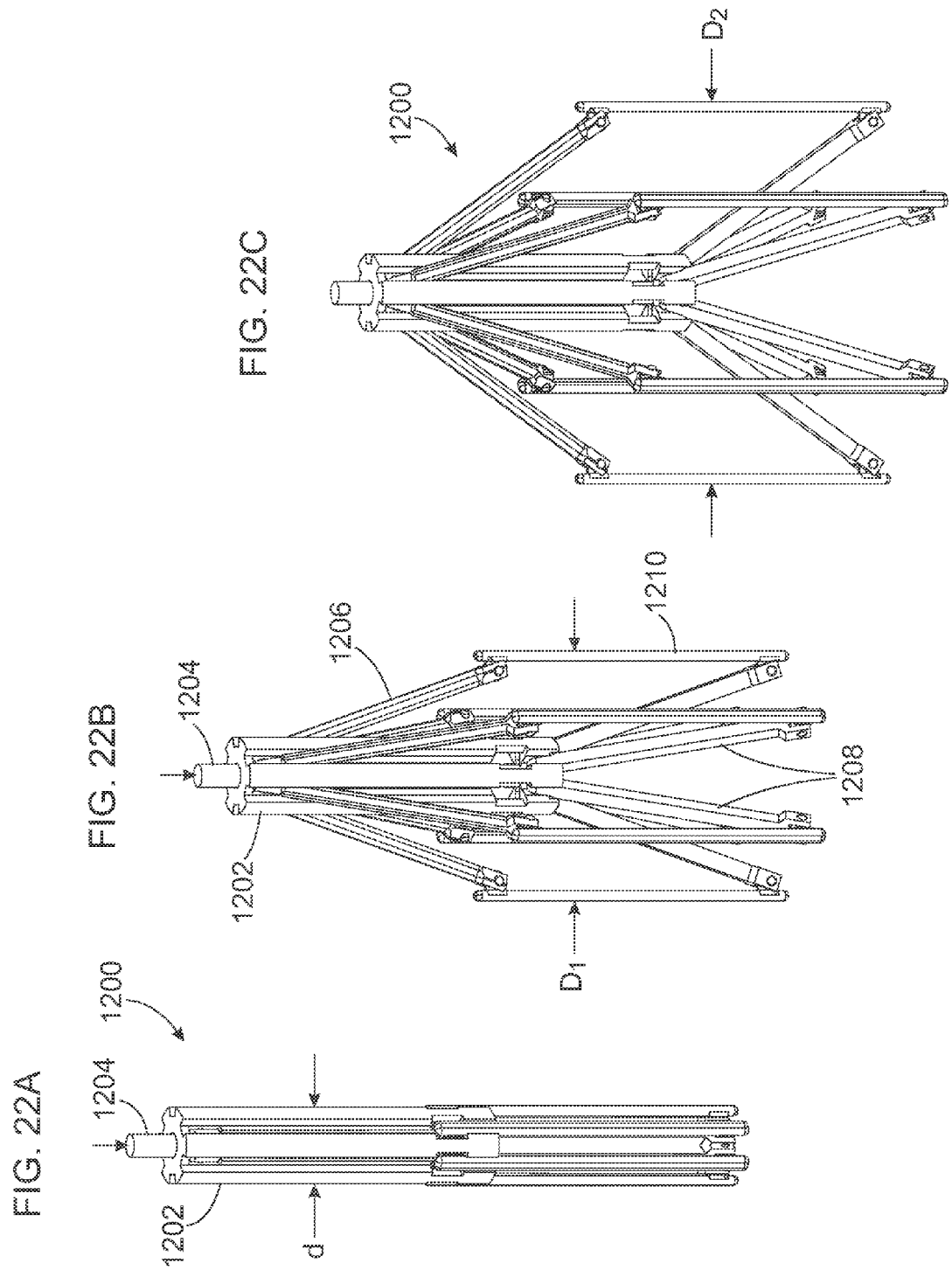

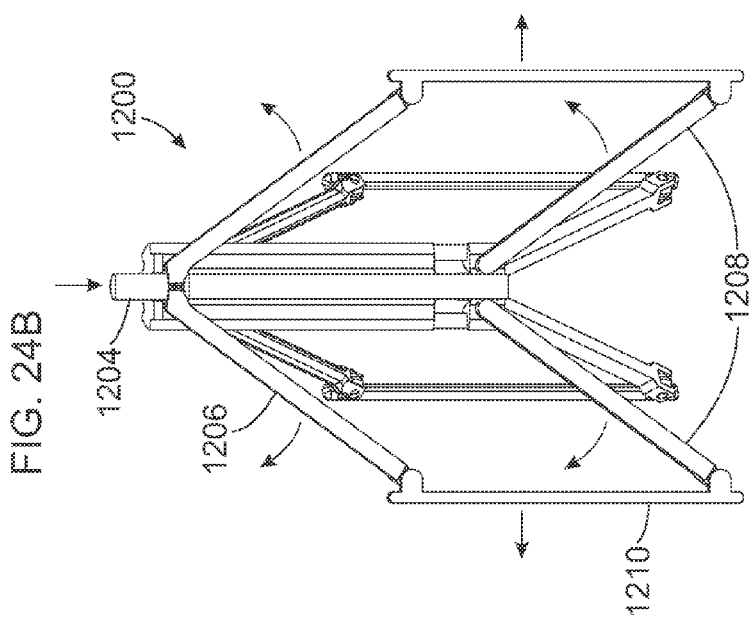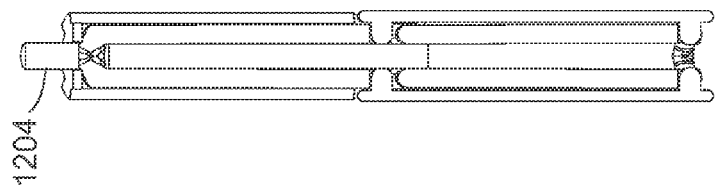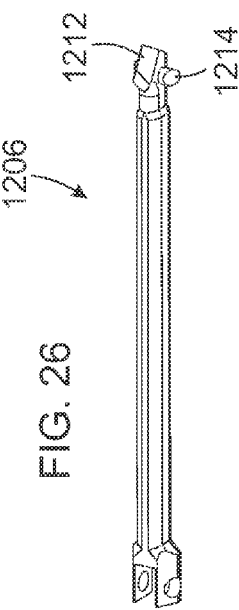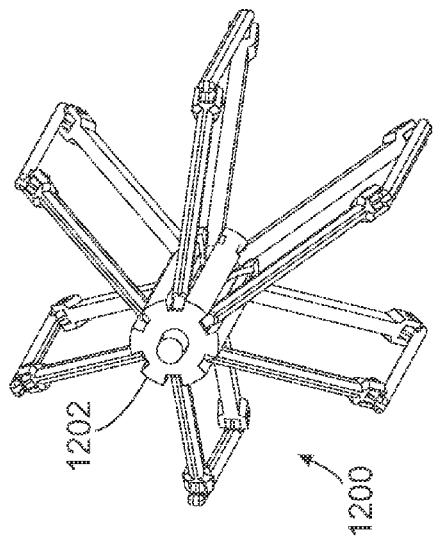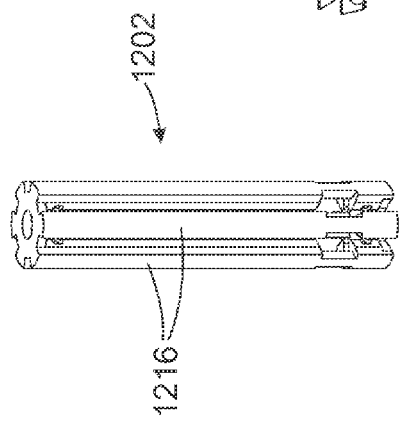

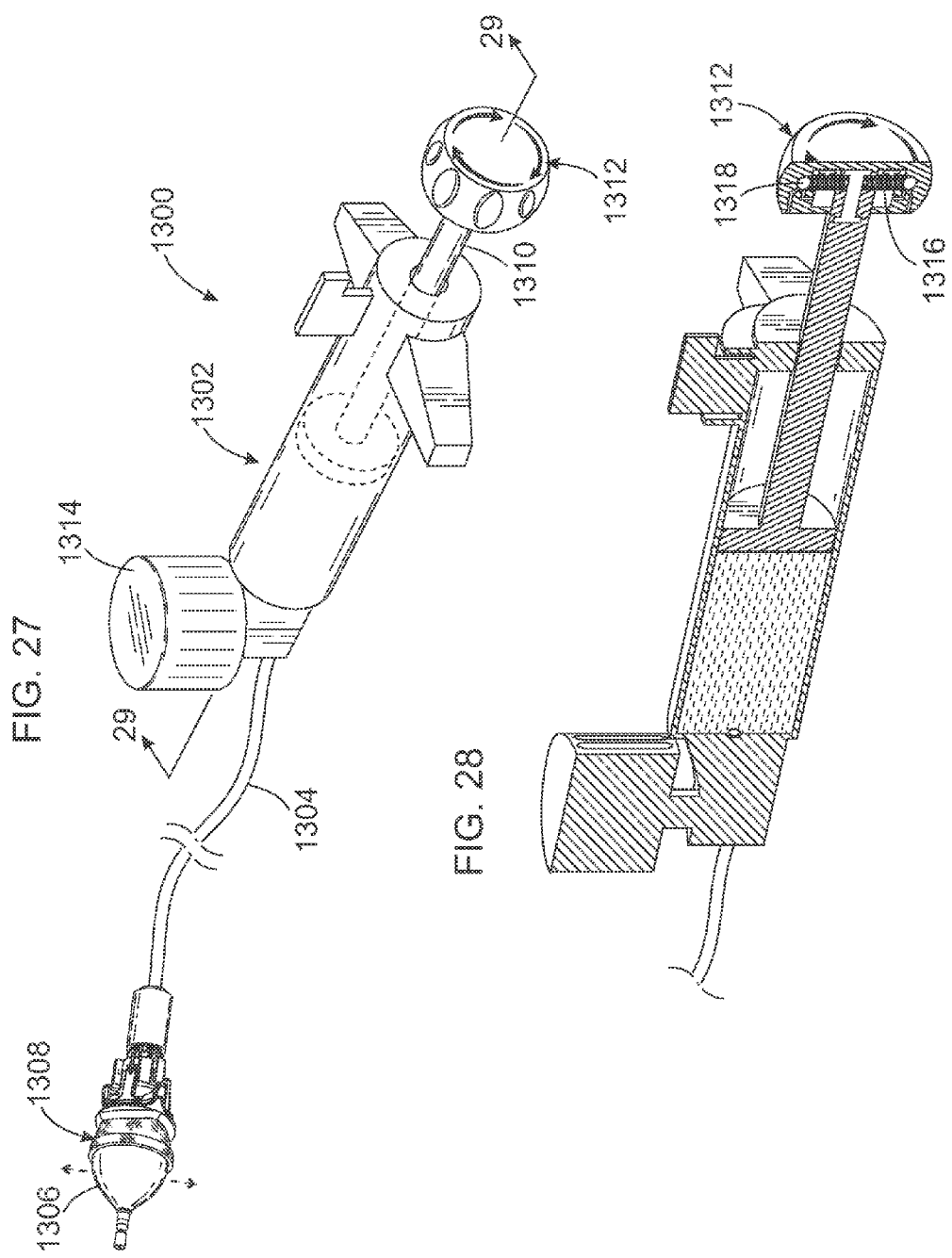

FORCE-BASED HEART VALVE SIZER

RELATED APPLICATIONS

The present application claims priority under 35 U.S.C. §119 to U.S. Provisional Application Ser. No. 61/568,913, filed Dec. 9, 2011.

FIELD

The present disclosure is directed to methods and apparatus for determining a size of a valve annulus. More particularly, the present disclosure relates to a heart valve sizer.

BACKGROUND

Replacement of a diseased or malfunctioning cardiac valve requires accurate sizing of the valve annulus. After the diseased or malfunctioning cardiac valve has been removed, the surgeon measures the patient's valve annulus to determine the appropriate replacement valve size.

A conventional system for measuring a patient's valve annulus includes a number of varying size discs, which can be removably or fixedly attached to a rod. The size of each of the discs corresponds to an available valve size. The surgeon inserts the disc into the patient's valve annulus and checks the fit of the disc within the valve annulus. If the surgeon is not satisfied with the fit, the surgeon removes the disc from the body and inserts a new disc into the valve annulus. The size of a patient's native heart valve annulus is determined by inserting sizers of various diameters until the surgeon determines which one feels correct. This is a time-consuming method since for each valve size the surgeon inserts, the surgeon must remove one of the discs and try another one. This procedure increases the overall surgery time which increases the risk to the patient and also increases the cost of the procedure. Further, the determination of the appropriate size is based on the feeling of the surgeon rather than any mechanical feature. This determination based on the feeling of the surgeon may not be accurate. Thus there is a need for a sizer that is accurate in determining the size of the annulus of a valve.

Alternatively, a heart valve sizer may be used which is introduced into the patient only once, and the same sizer is capable of gauging a number of appropriate valve sizes. However, these sizers are dimensionally the same as the valves they represent. Due to size constraints, insertion of the heart valve sizers may be a hindrance for certain procedures, especially for minimally invasive surgical incisions such as thoracotomies. With minimally invasive surgical (MIS) type procedures performed through small surgical incisions, the surgeon may not have a good approach angle to the native annulus, thus hindering an accurate tactile feedback to the surgeon when the sizer is in place.

Additionally, it is essential for the replacement heart valve to be of the right fit. In determining the optimal replacement device for a diseased heart valve, a surgeon generally exerts some level of force to determine a tight fit size. Each surgeon may have a different definition of a tight fit and what is the optimal force that may be exerted. Also, excessive force if applied may result in inaccurate sizing of the annulus, or even tissue damage. Also, traditional valves involve parachuting the valve down to the annulus with 12 to 14 sutures, and thus sizing is somewhat less sensitive. However, newer valves sometimes employ only three or in some cases no sutures making sizing accuracy more challenging. It is more difficult to avoid paravalvular leaks and risk of embolization if three or no sutures are used and there is a sizing mistake.

Given the above limitations, it is desirable to have a single, one-size-fits-all sizer which could be used to quickly and accurately determine the appropriate valve size for a patient's heart through a minimal sized incision. It is desirable to have a sizer that does not rely entirely on the surgeon's feel, but on a mechanism that consistently and more accurately determines the patient's annulus size.

SUMMARY

The embodiments of the present disclosure have several features, no single one of which is solely responsible for their desirable attributes. Without limiting the scope of the present embodiments as expressed by the claims that follow, their more prominent features will now be discussed briefly. After considering this discussion, and particularly after reading the section entitled "Detailed Description", one will understand how the features of the present embodiments provide advantages, which include providing an adjustable force-based heart valve sizer system that can be used to determine the size of patient's heart valve annulus using a single sizer through minimal size incision.

In one embodiment, an adjustable valve sizer is provided. The valve sizer includes an elongate shaft having a proximal end and a distal end with a movable sizing element coupled to the distal end of the shaft. A valve sizing portion has an outer dimension which is at least partially defined by the movable sizing element. An actuator assembly is provided at the proximal end for moving the movable sizing element so that the valve sizing portion corresponds to the various valve sizes.

In a preferred device, a heart valve sizer for determining an appropriate replacement prosthetic heart valve size when performing a valve replacement procedure comprises a proximal actuator, a shaft extending distally from the actuator and having a movable member and a stationary member, and a sizing element coupled to the distal end of the shaft. The sizing element has a hub and a plurality of petals each radially movable between a first retracted position and a second expanded position. The hub is fixed to the stationary member in the shaft and the petals are connected to expand radially upon displacement of the movable member in the shaft. A clutch mechanism connected between the actuator and the movable member in the shaft transmits movement forces therebetween, wherein movement of the actuator causes displacement of the movable member and consequently outward radial expansion of the petals in the sizing element into contact with a surrounding heart valve annulus. The clutch mechanism slips at a predetermined reaction force imparted by the heart valve annulus against further outward radial expansion of the petals.

A preferred method of sizing a patient's cardiac valve annulus disclosed herein comprises the steps of:

providing a valve sizer having a shaft with a proximal end and a distal end and an expandable sizing element coupled to the distal end of the shaft, the sizing element being radially expandable between a first retracted position and a second expanded position, the valve sizer further having an actuator assembly comprising an actuator that moves relative to a handle, a clutch ring mounted at the proximal end of the shaft and coupled for rotation to the actuator via a clutch mechanism, and a stationary rod extending through at least a portion of the shaft, wherein the shaft is connected to the clutch ring so that movement of the actuator transmits through the clutch mechanism to the clutch ring and shaft and causes axial movement of the shaft, wherein the axial movement of the shaft causes radial expansion of the sizing element;

inserting the valve sizer in the first retracted position into the patient so that the movable element is positioned within the valve annulus; and rotating the handle until the clutch mechanism of the actuator assembly begins to slip indicating that the sizer has fully engaged the annulus.

In both the preferred device and method, shaft preferably comprises a rod extending through a hollow shaft and the actuator comprises an actuator ring, where the rod is the stationary member fixed with respect to both the handle and the hub, and the hollow shaft is fixed with respect to a clutch ring that is coupled for rotation to the actuator ring via the clutch mechanism. In this configuration, the clutch ring is connected via a screw thread to the stationary handle so that rotation of the clutch ring causes axial movement of the hollow shaft. The clutch mechanism may comprise a plurality of bearings biased by springs into detents. The plurality of bearings and the springs are desirably held within the clutch ring and the detents are formed on an inner surface of the actuator ring.

In one version, the plurality of sizer petals move in a plane substantially perpendicular to a longitudinal axis defined by the shaft. The movable member may move axially along the shaft and contact and pivot a lever for each of the petals, wherein pivoting of the levers causes radial expansion of the petals. Or, the movable member may move axially along the shaft and connect to a camming member that directly contacts and causes radial expansion of the petals. The plurality of petals may define a cylindrical annulus portion and an outwardly-extending flange on a proximal end of the cylindrical annulus portion, and the outwardly-extending flange may have an axially undulating peripheral shape.

In a percutaneous version, the sizer is configured for delivery through a catheter and the petals in their first retracted position limit the diameter of the sizing element to be small enough to enable passage through the catheter, and the petals remain parallel to an axis of the hub while being displaced outward.

In another embodiment, a force feedback-based heart valve sizer is provided. A force feedback-based sizer provides a calibrated force indication that allows the surgeon to apply the optimal (or at least a known) level of force. The force feedback-based sizer provides tactile and visual feedback to the surgeon that a desired force has been reached. The force feedback-based sizer may additionally measure the force applied and display the value. It may further comprise a force limiter, or clutch, that prevents forces above a pre-determined level from being transmitted through to the sizer.

These and other features will become apparent with the following description of the preferred embodiments.

BRIEF DESCRIPTION OF THE DRAWINGS

The embodiments of the present disclosure will now be discussed in detail with an emphasis on highlighting the advantageous features. These embodiments depict the novel and non-obvious features shown in the accompanying drawings, which are for illustrative purposes only. These drawings include the following figures, in which like numerals indicate like parts:

FIGS. 1A-1C show a perspective view of a heart valve sizer with a sizing element having sizing petals in radially expanded positions, according to one embodiment;

FIG. 1D shows the heart valve sizer with the sizing element, and the sizing petals in radially retracted positions;

FIGS. 2A-2C show cross sectional views of an actuator assembly for the various sizing elements disclosed herein;

FIGS. 4A and 4B show an alternative actuator assembly exploded and assembled with a sizing element having a hub cover;

FIG. 5A shows the sizing element with sizing petals in a semi-expanded position, and FIG. 5B is a cross section thereof;

FIG. 5C shows a petal and a hub assembly from the sizing element of FIG. 5A, while

FIGS. 6A and 6B are assembled and exploded views of an alternative sizing element of the present application;

FIGS. 7A and 7B are sectional views through an alternative actuator assembly and sizing element having a conical camming hub;

FIG. 7C shows a ratchet mechanism for use in the actuator assembly of FIG. 7A;

FIG. 8A shows the sizing element coupled at the distal end of a shaft with sizing petals in a retracted position;

FIG. 8B shows a cross-section along lines A-A' of the sizing element of FIG. 8A;

FIG. 8C shows an individual sizing petal;

FIGS. 17A-17B show a force feedback-based heart valve sizer, according to yet another embodiment;

FIGS. 18A-18B show a heart valve sizer with a flexible coil;

FIGS. 19A-19E show a heart valve sizer with stackable valve hubs;

FIGS. 22A-22C show a catheter-based sizing element in accordance with the present application in several stages of expansion;

FIGS. 23 and 24A-24B are further views of the catheter-based sizing element;

FIGS. 25 and 26 are enlarged views of two components of the catheter-based sizing element; and FIGS. 27 and 28 are schematic views of a balloon catheter inflation system that utilizes a clutch-limiter as described herein to limit the maximum inflation pressure.

DETAILED DESCRIPTION

Figure 1B:
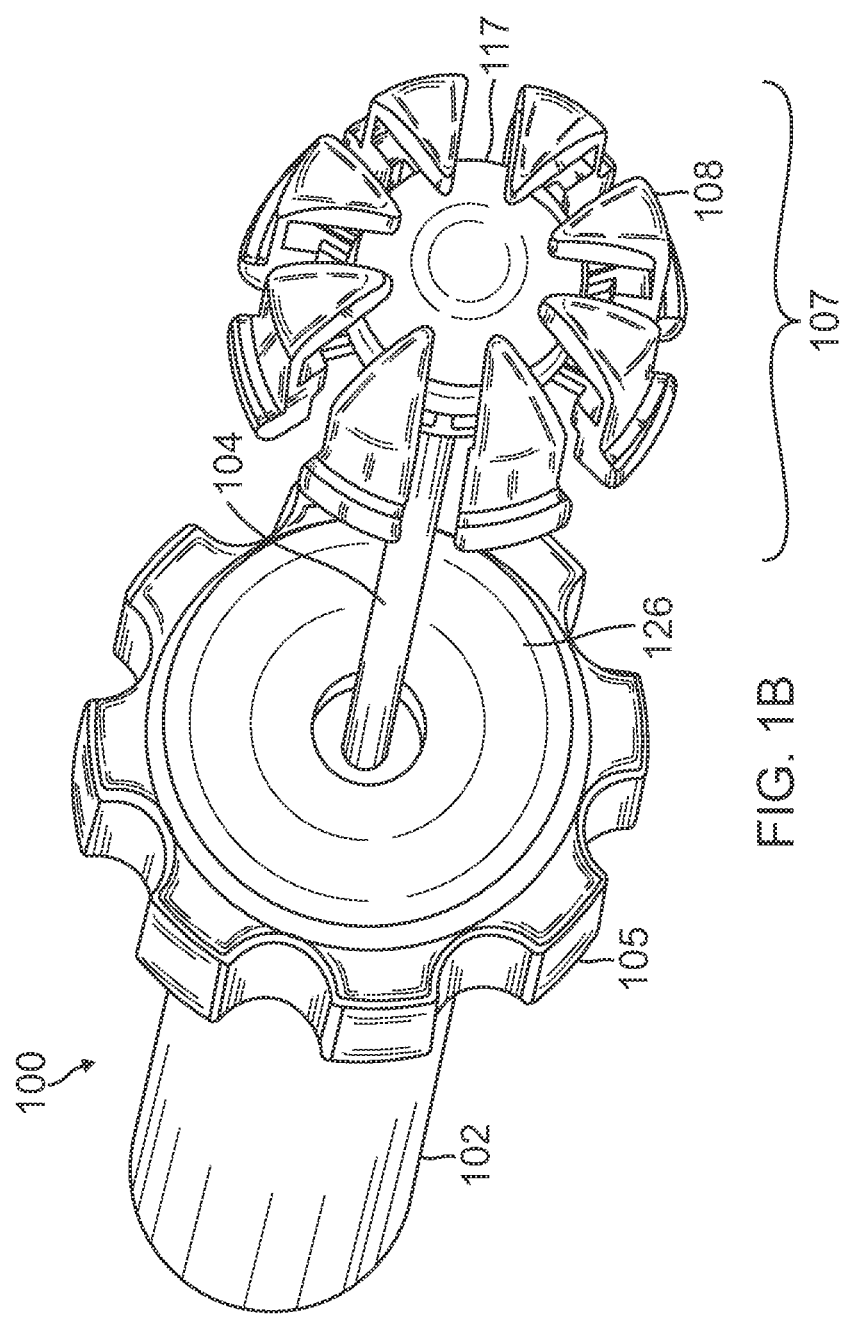

Referring to FIGS. 1A-1D, a first valve sizer 100 is shown. The valve sizer 100 includes an elongate hollow shaft 104 extending along the length of the sizer. An actuator assembly 106 is coupled to the proximal end of the shaft 104, while a radially expandable sizing element 107 is coupled to the distal end. The shaft 104 is preferably malleable ensuring that it is flexible enough to allow the sizer 100 access to the annulus from different angles, or through curved or bent access passages. The handle 102 is preferably static and is used for keeping the valve sizer steady in the hands of the operator.

With reference to FIGS. 1C and 2A-2C, the actuator assembly 106 includes an actuator 105, a handle 102, a clutch ring 121 (also referred to as ring 121), and a clutch cover 126 mounted within the actuator 105. The handle 102 threadingly engages a tubular threaded portion 121B ending axially up from the ring 121 which, in turn, is mounted to the shaft 104. Rotation of the clutch ring 121 relative to the handle 102 causes axial displacement therebetween. The handle 102 is used for positioning the radially expandable sizing element 107 on the end of the shaft 104 within the annulus. As will be seen, rotation of the actuator 105 and clutch ring 121 expands and retracts the radially expandable sizing element 107 so that the valve sizing portion corresponds to various valve sizes, as will be discussed in detail below.

Figures 1C, 1D:
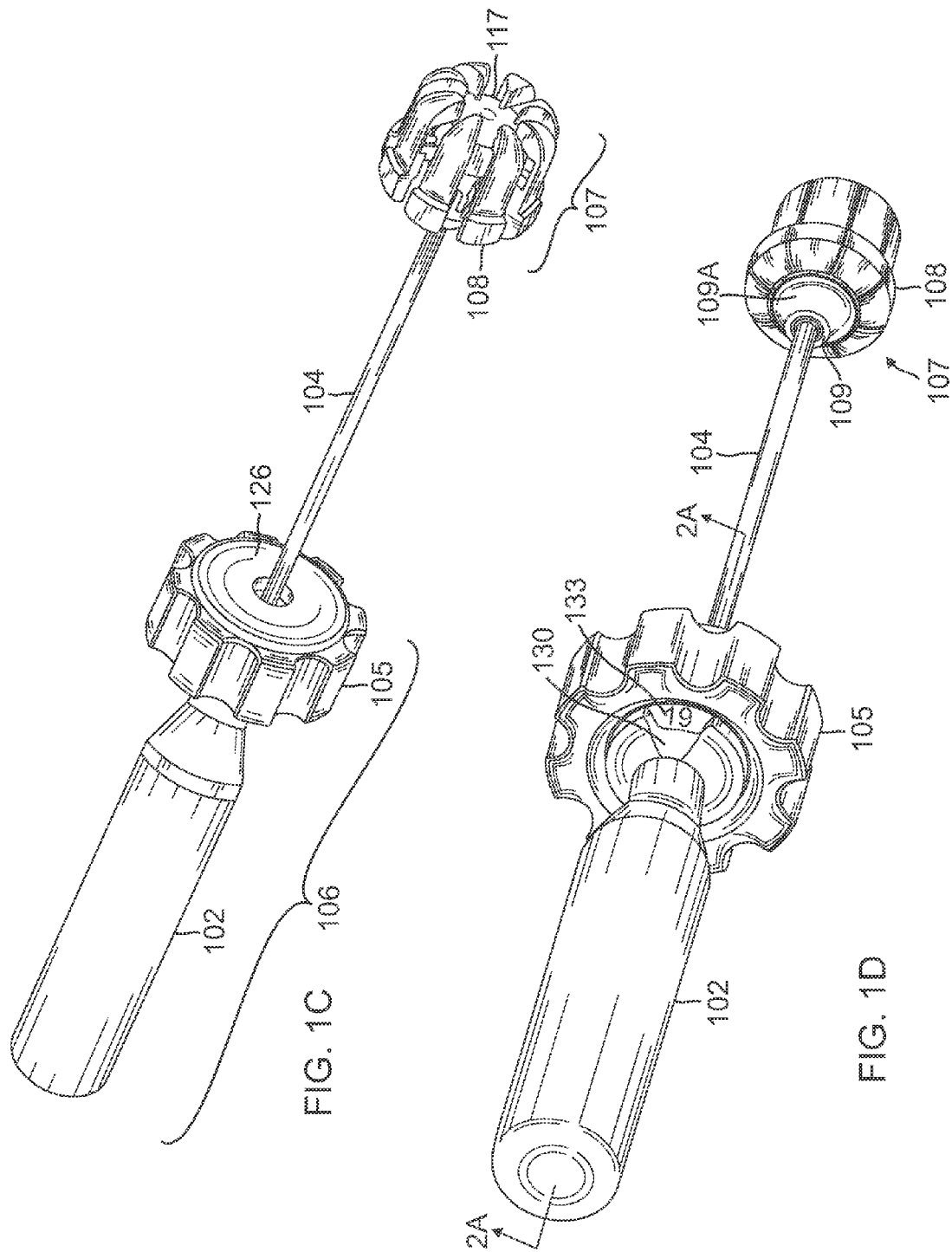

The radially expandable sizing element 107 defines an outer dimension of the valve sizing portion. The sizing element 107 has a hub 117 with a number of sizing petals 108 that extend radially outward from the hub 117 and are mounted to move radially in and out. Figures 1A-1C illustrate the sizing petals 108 in radially expanded positions while FIG. 1D illustrates the sizing petals 108 in radially retracted positions. Rotation of the actuator 105 controls the radial expansion of the sizing petals 108 from the retracted position to the expanded position as will be described below.

Figure 3A:
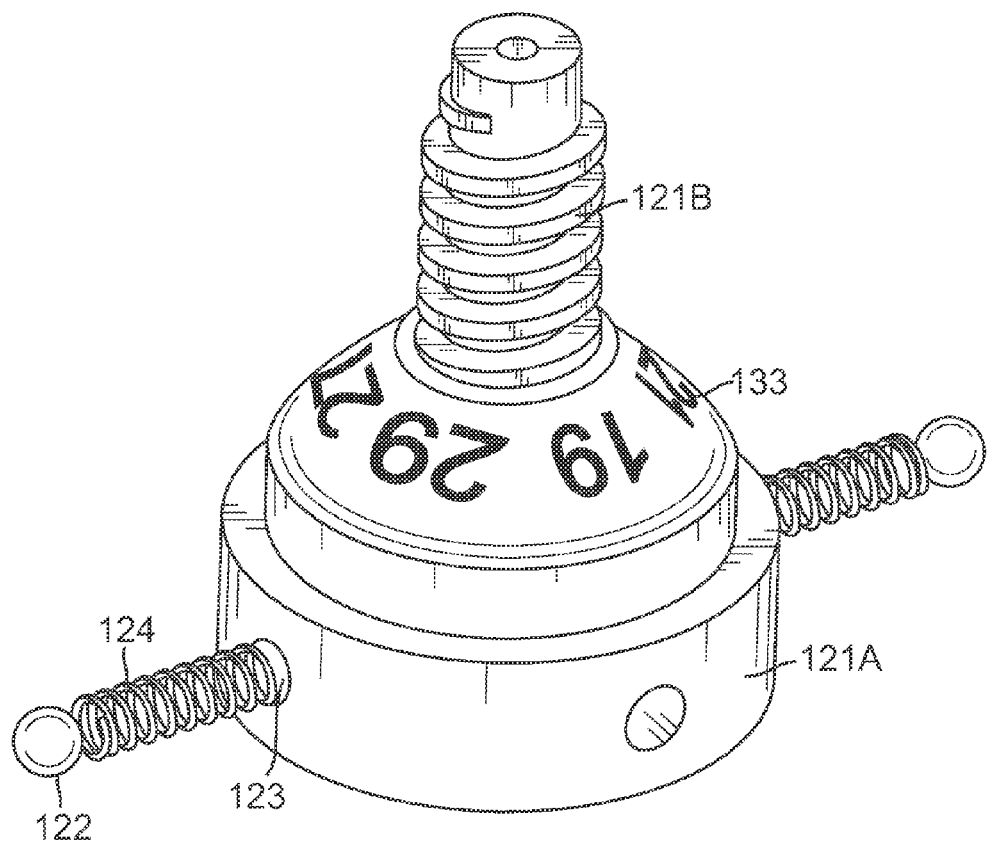
FIGS. 3A-3B show an alternative clutch ring with valve size markings according to one embodiment for use in the actuator assemblies disclosed herein.
Figure 3B:
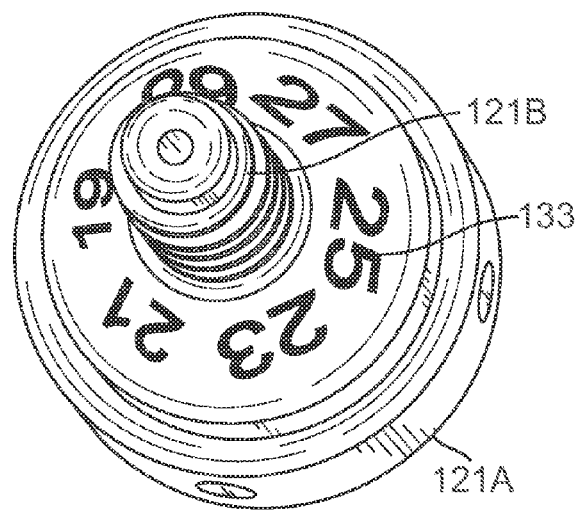

As best seen in FIG. 1A and also in FIG. 1D, the distal end of the handle 102 has a window 130 which shows a number of numerical markings 133 on the ring 121 indicating the size of the valve sizer. The ring 121 has a circular base 121A with markings 133 (see FIGS. 3A and 3B) for indicating the valve size, and the tubular threaded portion 121B extending laterally in the handle. Rotation of the actuator 105 rotates the clutch ring 121 and markings 133 thereon past the window 130 until a predetermined torque limit is reached, at which point a clutch mechanism slips, as will be explained, and further rotation of the actuator 105 is decoupled from the ring 121. The valve size corresponding to the torque limit is displayed in the window 130. In other words, the actuator 105 continues to expand the sizing element 107 outward until it contacts the surrounding annulus, at which point the resistance imparted to the sizing element 107 transmits back through the clutch mechanism, decoupling rotation of the actuator 105 from the clutch ring 121.

Figure 3C:
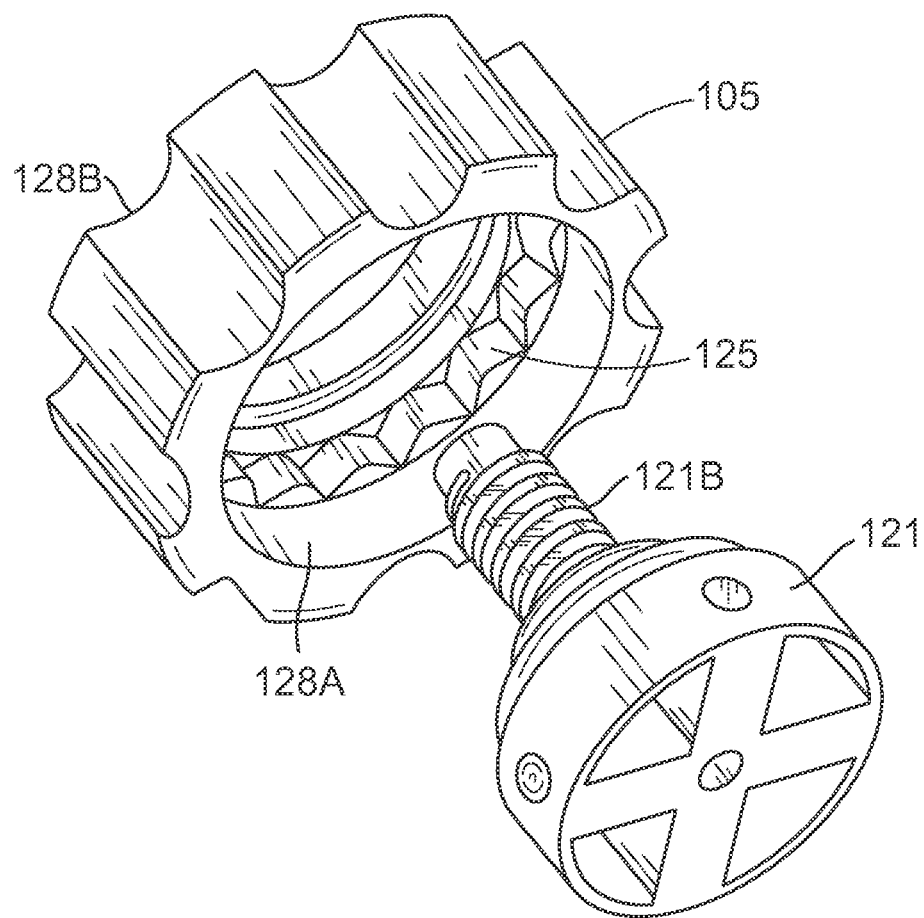
FIG. 3C shows an exploded view of an actuator assembly including an actuator ring and the clutch ring of FIGS. 3A-3B.

FIGS. 2A-2C show various cross-sectional views of the actuator assembly 106. FIG. 3C shows an exploded view of the actuator 105 and the ring 121. Ring 121 is inserted in the actuator 105 where the tubular threaded section 121B extends from the top recess 128A towards the bottom recess 128B. FIG. 4A shows an exploded view of the actuator assembly 106 mounted on the shaft 104. A clutch cover 126 snap fits on the actuator 105 over the clutch ring 121.

With reference again to FIGS. 1C and 2A-2C, the actuator assembly 106 comprises the actuator 105 having a top recess 128A and a bottom recess 128B. The handle 102 engages the tubular threaded portion 121B on the clutch ring 121 within the actuator top recess 128A. The clutch ring 121 is fixed with respect to the hollow shaft 104, while the handle 102 mounts to a fixed length cable or rod 120 extending laterally through the shaft 104. The length of the cable or rod 120 extending between the hub 117 and the handle 102 is fixed, and in this sense the rod 120 forms a stationary member between the handle 102 and the hub 117.

As seen in FIG. 2C, a stepped washer 140 abuts the lower end of the clutch ring 121 towards the bottom recess 128B of the actuator 105 and mounts such as with adhesive to the shaft 104. A clutch cover 126 snap fits over the clutch ring 121, and threads within the actuator 105, and therefore locks the washer 140 and the ring 121 within the actuator 105 at the bottom recess 128B of the actuator. The washer 140 is captured between the lower cover 126 and the lower surface of the clutch 121A, and along with the shaft 104 moves distally and proximally with the actuator mechanism.

FIG. 2B shows the ratchet mechanism for the ring 121 according to one embodiment. As will be described below, the shaft 104 attaches to a mechanism that expands the sizer 100 and is coupled to the clutch actuator 105 by a ratcheting mechanism. As seen also in FIG. 3A, a cylindrical base 121A of the ring 121 has springs 124 inserted into or extending across at least one diametric hole 123. Spring-loaded bearings 122 seat into a series of cutouts or detents 125 formed on an inner surface of the surrounding actuator ring 105. Rotation of the actuator ring 105 thus rotates the clutch ring 121 until the bearings 122 slip from the detents 125 against the force of the springs 124.

The clutch ring 121 and the actuator 105 function as a ratcheting mechanism such that when a predetermined amount of torque is applied, the actuator 105 ratchets and does not drive the shaft 104 any further. Therefore, the size of the annulus is determined by rotating the actuator 105 until the ring 121 begins to ratchet. The actuator 105 is coupled to the ring 121 such that the rotation of the actuator 105 causes the shaft 104 to move. The force needed to overcome the ratchet mechanism is set to correspond to the reaction force being applied to the sizing petals by the annulus being sized. That is, the reaction force imparted by the annulus to the sizer as the sizer expands gradually increases until the sizing petals fully engage the annulus. The reaction force creates a reaction torque in the shaft 104 which will eventually overcome the springs 124 in the ratchet mechanism such that the clutch slips. The markings 133 indicate an outer diameter of the annulus. The torque at which the clutch slips may be calibrated to match a particular reaction force experienced by the sizing element 107, such as by varying the spring force or number or character of the bearings 122, springs 124, and detents 125.

Also, although it is preferred to use the rotating actuator 105 to move the sizing petals 108, any other actuation mechanism may be used including a trigger, sliding lever, or scissors-type actuator 106. The hollow shaft 104 forms a movable member between the handle 102 and hub 117, and transmits the force needed to operate the petals 108. Other movable members are possible, and the movement need not be linear but could also be rotational. Essentially, there is a stationary member (e.g., rod 120) that holds the hub 117 from moving relative to the handle, 102, and a movable member (e.g., the shaft 104) that transmits the driving force from the handle to the hub to operate the petals 108, and a variety of such mechanisms are within the scope of the present application.

The ball-spring-detent type of clutch mechanism is preferred in the heart valve sizing context as sensitivity to environmental factors is relatively low. That is, the accuracy of the torque limit is known with a high degree of accuracy and is not affected by temperature, fluids such as blood, etc. Repeatable results in the operating room make such a clutch system preferable to one which relies on frictional forces, as the coefficient of friction of the contact surfaces may change when subjected to a wet environment, temperature fluctuations, or after being sterilized.

Details of the components and function of an exemplary sizing element 107 will now be described. FIG. 4A shows the actuator assembly 106 mounted on the shaft 104, which terminates in an actuation bearing 109. FIG. 4B shows the shaft 104 and actuation bearing 109 positioned just proximal to the sizing element 107. As will be explained, axial displacement of the actuation bearing 109 within the sizing element 107 causes radial movement of the petals 108 via a camming and linkage system shown best in FIGS. 5A-5D.

Figure 5C:
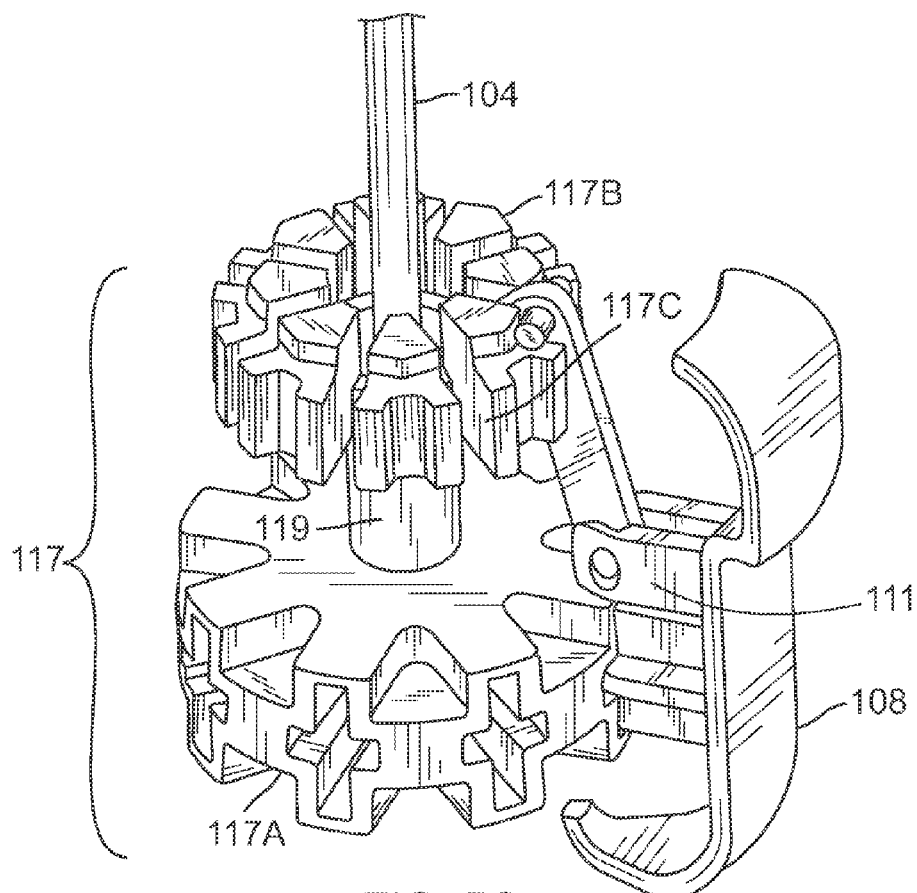

As seen in FIGS. 5B and 5C, the hub 117 includes a top portion 117B and a bottom portion 117A connected through a shaft stub 119, which extends through the top portion 117B to the bottom portion 117A of the hub. As seen in FIG. 5B, the fixed length cable or rod 120 extends into and is fastened within the shaft stub 119, and thus the hub 117. In this way, the distance between the handle 102 and hub 117 remains constant. The top portion 117B and the bottom portion 117A include a plurality of features, such as slots 117C in the top portion 117B, splaying outward around a central axis for interacting with the linkages for moving the petals 108.

The camming assembly further comprises a hub cover 109A that snap fits to the hub 117, and the actuation bearing 109 extends through the hub cover 109A and fits within a bore in the top portion of the hub 117B. As seen in FIGS. 4B and 5B, the actuation bearing 109 has a distal end 109B and a proximal end 109C. The hub cover 109A rests over the proximal end 109C of the actuation bearing 109. The distal end 109B of the actuation bearing 109 is shaped like a disc. Actuation bearing 109 is coaxially placed around and fastened to the hollow shaft 104, and is aligned with the shaft stub 119 of the hub 117. Both the hollow shaft 104 and actuation bearing 109 slide over the rod 120, which again is anchored in the hub 117. Displacement of the hollow shaft 104 thus displaces the actuation bearing 109 relative to the hub 117.

Figure 5D:
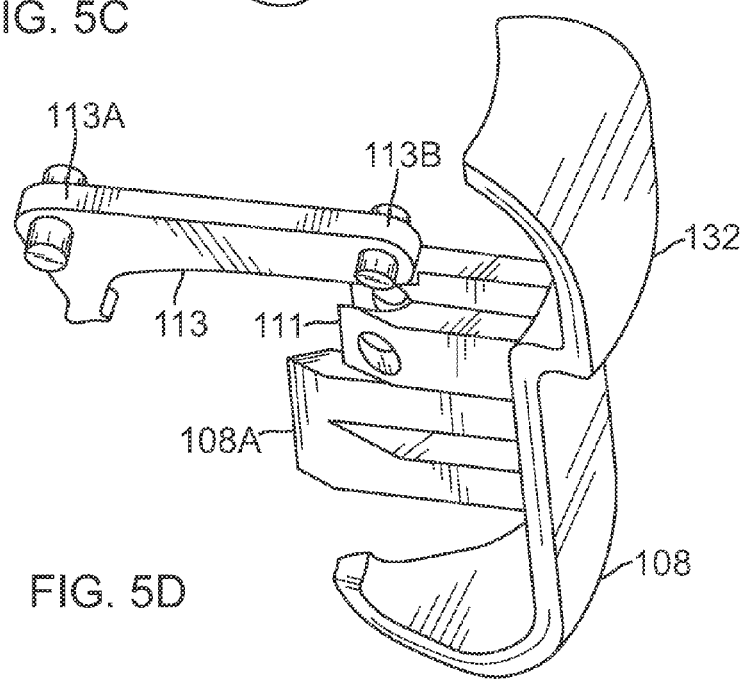
FIG. 5D shows a single petal and a lever that links the petal to the hub.
Figure 9A:
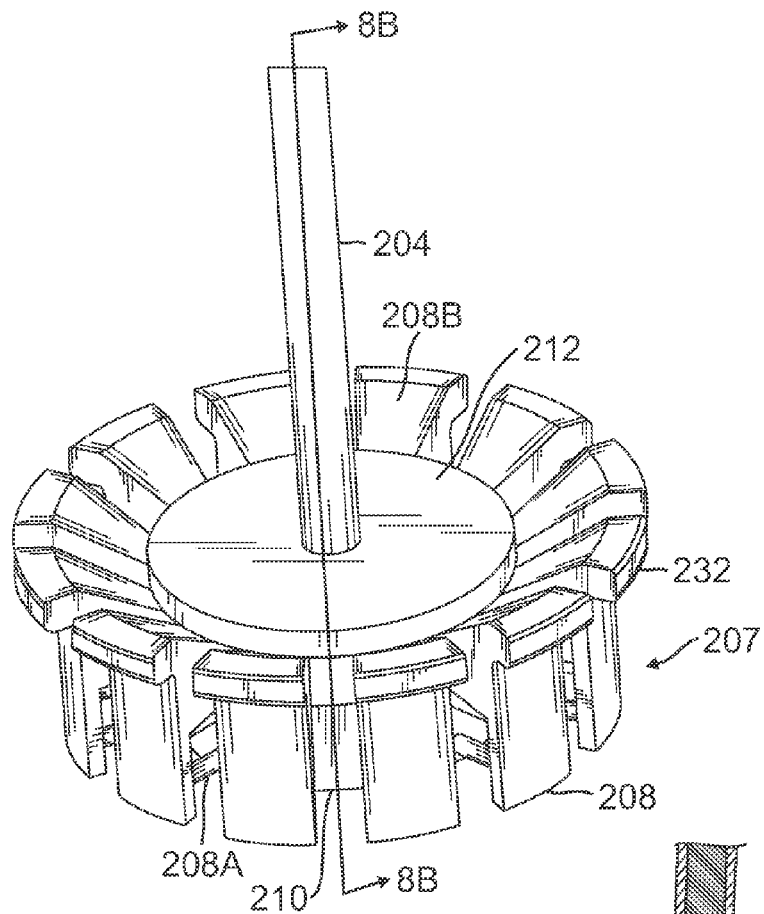
FIG. 9A shows the sizing element with sizing petals in an expanded position.
Figure 9B:
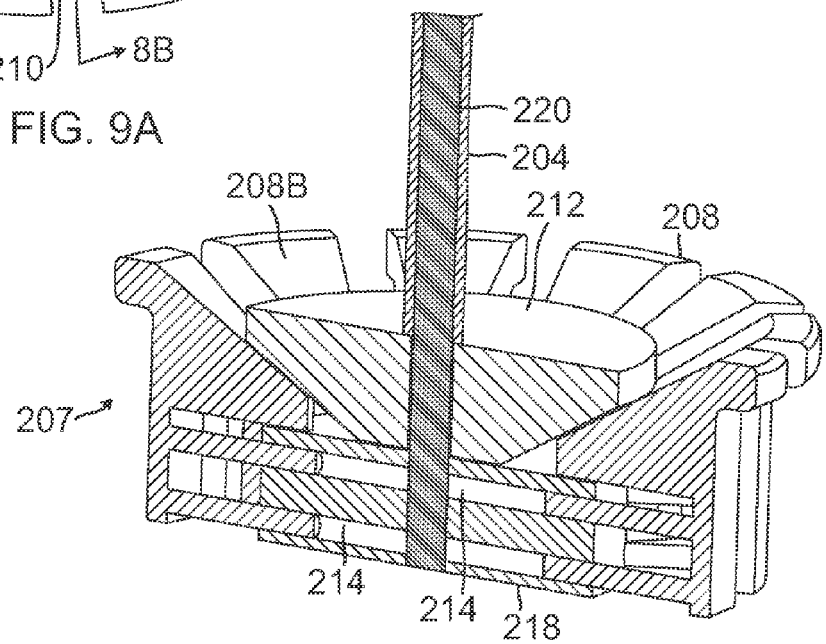
FIG. 9B shows a cross-section along lines B-B' of the sizing element of FIG. 9A.

The camming assembly includes a number of levers 113 for coupling the petals 108 with the hub 117, seen for one petal in FIG. 5D. The number of levers 113 corresponds to the number of petals 108. Proximal ends 113A of the tapered lever 113 extend through the slots 117C of the hub 117. As seen in FIG. 5B, a finger 113C of the lever 113 extends into an annular groove 109D (FIG. 5A) between the distal end 109B and proximal end 109C of the actuation bearing 109. An outer end 113B of each lever 113 is connected, such as via a journal pin, to a bifurcated pair of inwardly-extending arms 111 on the sizing petal 108, as seen in FIG. 5C. FIG. 5D shows the coupling of the lever 113 with the petal 108, where the distal end 113B of the lever 113 couples with the inwardly-extending arms 111. Rotation of the actuator 105 ultimately leads to axial movement of the shaft 104 and actuation bearing 109. Axial movement of the actuation bearing 109 causes movement of the lever 113 by virtue of the camming interaction between the annular groove 109D and the lever finger 113C. The distal end of the 113B pivots outward from distal movement of the actuation bearing 109, thus causing radial expansion and retraction of the petals 108. The converse is true also, wherein proximal retraction of the shaft 104 and actuation bearing 109 constricts the petals 108 radially inward, thus reducing the profile of the sizing element 107 to facilitate removal from the native annulus after a sizing procedure.

FIGS. 6A and 6B illustrate a modified sizing element 107' much like the previously-described element 107, and as such like parts will be given like numbers with a prime designation. The sizing element 107' has a plurality of petals 108' that constrict about a hub 117' into a first, reduced diameter configuration as seen in FIG. 6A. In contrast to the earlier petals 108, each modified petal 108' has a proximal flange that in aggregate defines an undulating or scalloped peripheral flange 112. More particularly, adjacent petals 108' have either a convex up flange 112A or a concave up flange 112B, as seen best in the exploded view of FIG. 6B. Preferably, there are six (6) petals 108' with three having a convex up flange 112A and three having a concave up flange 112B. The aggregate flange 112 therefore defines an undulating peripheral shape with three peaks and three valleys, mimicking the natural contours of an aortic annulus and the shape of the sewing ring of a prosthetic heart valve, where the peaks correspond to the commissures and the valleys to the cusps in between. Provision of the scalloped peripheral flange 112 helps the surgeon properly seat the sizer down into the aortic annulus so that the cylindrical body formed by the petals extends fully within and accurately reflects the size of the annulus orifice.

The petals 108' also have slightly modified inwardly-extending arms 111' which have pointed inner ends for ease of assembly with the distal ends of the levers 113' and into the receiving channels formed in the bottom portion 117A' of the hub 117'. The pointed inner ends also provide maximum overlap between the internal radial channels in the hub 117' and the petals 108', which is especially important at full expansion for larger annuluses (e.g., 29 mm). Additionally, the actuation bearing 109' has axial ribs that mate with axial grooves in the hub cover 109A' to prevent relative rotation therebetween. Aside from the aforementioned modifications, the sizing element 107' functions in the same way as the earlier-described element 107, and thus will not be further described.

A method of selecting an appropriate valve size is now described with reference to the aforementioned figures. In a minimally invasive procedure, the valve sizer 100 is preferably introduced into the patient between adjacent ribs in the patient without cutting or significantly deflecting the ribs. At least one dimension of the delivery profile of the retracted valve sizer 100 is such that it is no more than 19 mm, and more preferably no more than 17 mm, so that the valve sizer 100 can be easily introduced between adjacent ribs in the patient. The surgeon then positions the sizing petals 108 in the valve annulus and rotates the actuator 105 until the sizing petals 108 contact the valve annulus. The actuator 105 is rotated until the ratchet begins to slip thus indicating that the sizer has fully engaged the annulus and that a predetermined amount of force is being applied. When in the expanded position, the outer surfaces of opposing sizing petals 108 preferably have a maximum outer dimension of at least 29 mm and more preferably at least 33 mm. The surgeon then reads the appropriate valve size using the markings 133 that appear in the window 130 of the actuator. Following the sizing of the annulus, the actuator 105 is then rotated again so that the sizing petals 108 moves into the retracted position (as shown in FIG. 1D) for removing the valve sizer 100 from the patient.

When in the retracted position, the maximum outer dimension of the valve sizer 100 is preferably no more than 17 mm, more preferably no more than 18 mm, and most preferably no more than 19 mm. The preferred dimensions of the valve sizer 100 in the retracted position permits insertion of the valve sizer 107 between adjacent ribs in a patient when performing a minimally invasive valve procedure. For minimally invasive surgery approaches, the valve sizer could be made to collapse smaller than 17 mm, as described below with respect to FIGS. 22-26.

In another embodiment shown in FIG. 7-14, a disc that directly cams the sizer petals outward is provided instead of a lever arm assembly. FIGS. 7A and 7B show a proximal handle 202 that is rigidly connected to a distal hub 210 via a fixed-length cable or rod 220. An actuator assembly including an actuator ring 205 causes axial displacement of a hollow shaft 204 surrounding the rod 220, a distal end of the hollow shaft being fixed to a camming disc 212. More particularly, the hollow shaft 204 has a series of inner threads that cooperate with external threads on the rod 220 such that rotation of the shaft 204 relative to the handle 202 and rod 220 displaces the shaft and attached camming disc 212. The camming disc 212, in turn, directly acts on a plurality of sizing petals 208 of a sizing element 207 to convert them from a first, reduced diameter configuration as seen in FIG. 8A to a second, expanded configuration as seen in FIG. 9A.

FIG. 7B shows a ratchet mechanism that interposes a clutch between rotation of the actuator ring 205 and the hollow shaft 204, according to one embodiment. As mentioned, the shaft 204 is attached to the disc 212 that expands the sizing element 207. The ratcheting mechanism uses bearings 222 biased outward by springs 224 held in bores in a clutch ring 221. The clutch ring 221, in turn, is fixed around the hollow shaft 204. The bearings 222 seat into detents on the inner surface of the actuator ring 205, much like the clutch embodiment described above. The force needed to overcome the ratchet mechanism is set to correspond to the force being applied to the petals by the annulus being sized. That is, the reaction force applied by the annulus to the sizer as the sizer expands is transmitted to a reaction torque against rotation of the hollow shaft 204 and clutch ring 221, and the force needed to overcome the ratchet mechanism is set to the force needed to size the annulus.

FIG. 7C shows a slight variation on the clutch mechanism, wherein the bearings 222 are biased inward by the springs 224 into detents formed in an outer surface of the hollow shaft 204. In this version, there is no need for a separate actuator ring 205 as the user manually rotates the clutch ring 221 directly.

Referring to FIGS. 8A-9B, according to one embodiment, the radially expandable sizing element 207 is shown. The hub 210 includes radial slots (or holes) 214 shown in FIG. 9B which guide radial in and out movement of the sizing petals 208 between the retracted and expanded positions. The shaft 204 is coupled to the actuator 205 via the clutch mechanism described above so that rotation of the actuator 205 rotates the shaft 204 and the disc 212 with respect to the rod 220. Rotation of the shaft 204 causes radial movement of the sizing petals 208 in the slots 214 of the hub 210 between the expanded and retracted positions. That is, distal axial displacement of the shaft 204 and affixed disc 212 forces the distal conical surface of the disc directly against the conical proximal faces 208B of the petals 208, thus camming them outward. The taper the proximal face 208B of each sizing petal, its shape and its dimensions conforms to the shape and dimensions of the disc 212.

In one embodiment, the disc 212 is conical in shape (FIGS. 8B and 9B), with the taper of the disc 212 matching the taper of the sizing petals 208. The disc 212 is shown by itself in FIG. 10 having an internally threaded an axial hole 216 that the threaded shaft 204 engages. The disc 212 moves axially up and down with the threaded hollow shaft 204 to which it is mounted. The axial movement of the disk 212 provides a camming action to force the sizing petals to move due to their matching tapers on the disc 212 and the inner surfaces 108B of the sizing petals.

Figure 11:
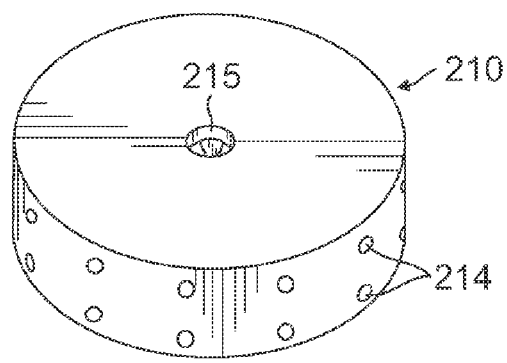
FIG. 11 shows one embodiment of the hub.

FIG. 11 shows the hub 210 by itself. The hub 210 has the radial holes 214 that correspond to pins 208A on the sizing petals 208, as seen in FIG. 8C. The central, axial hole 215 is to receive the threaded shaft 204. Each sizing petal 208 has at least one pin 208A that slides radially in the matching holes 214 in the hub 210. Preferably, each sizing petal 208 has at least two pins 208A that slide in the matching holes 214 of the hub 210 for better alignment. The number of pins 208A in each sizing petal 208 corresponds to the number of holes in that sector of the hub 210. The sizing petals 208 preferably have a curved outer surface 232 that together generally form a cylindrical peripheral shape when in the retracted and expanded positions. Taken together, the outer surfaces 232 of the sizing petals 208 define a valve sizing portion which engages the patient's valve annulus when sizing the replacement valve.

The device disclosed here shows a sizer with 8 sizer petals 208 which form a cylindrical sizer. More or fewer sizer petals could be used in the same way if it were deemed advantageous. Likewise, the shape of the sizer petals could be such that they form a sizer with a non-cylindrical shape.

Figure 12:
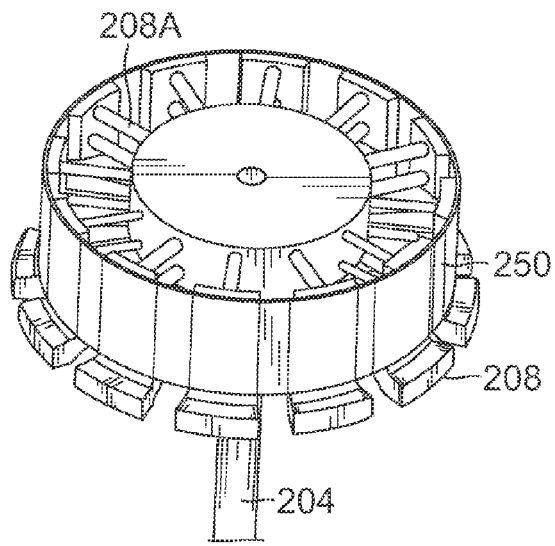
FIG. 12 shows a cylindrical sizing element with expanded petals covered with an extendable membrane.
Figure 10:
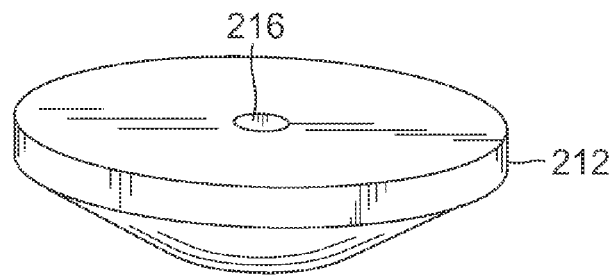
FIG. 10 shows the disc that cooperates with the hub in the sizers of FIGS. 8A-9B and 13A-14B.

In one embodiment, as shown in FIG. 12, the outside of the distal end of the sizer is covered by an extendible membrane 250 made out of a material such as silicone rubber. This would make the outside of the sizer smoother when expanded.

Figure 13A:
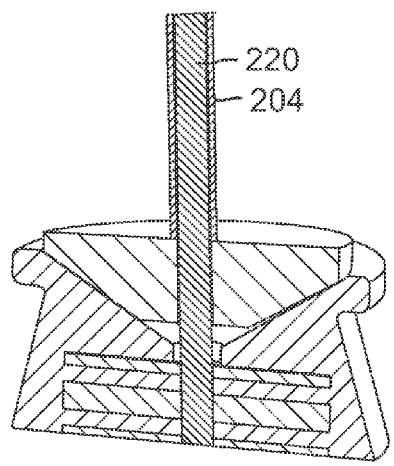
FIGS. 13A-13B show a tapered conical sizing element with petals in retracted and expanded positions, respectively, according to another embodiment.
Figure 13B:
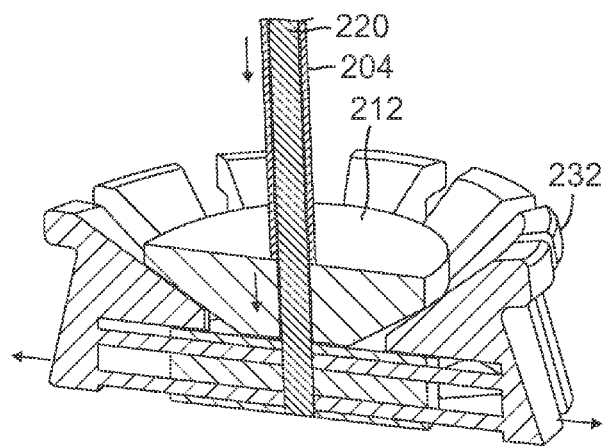
Figure 14A:
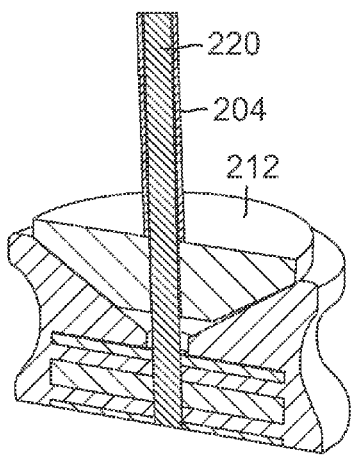
FIGS. 14A-14B show a concave shaped sizing element with petals in retracted and expanded positions, according to yet another embodiment.
Figure 14B:
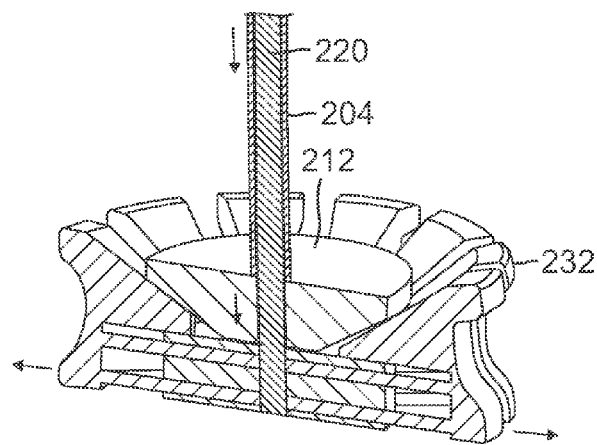

For instance, their shape could form a tapered conical shape. FIGS. 13A-13B show tapered conical petals 208 forming a tapered sizer. FIGS. 14A and 14B show a concave shaped sizer formed by petals 208 having concave outer surfaces. The concave shape of the sizer ensures that the sizer is properly engaged with the annulus. This may be especially beneficial in MIS procedures where visibility of the annulus is limited.

Up to now, clutch-based sizers have been described using a clutch mechanism with a pre-calibrated torque threshold. This is believed to provide excellent accuracy for a majority of patients and sizing procedures, especially using the relatively robust ball-detent clutch mechanism. However, certain sizing tasks may involve a high degree of variability or require a relatively fine force threshold determination which may not be satisfied by a pre-calibrated clutch having a single torque threshold. Consequently, the present application contemplates a number of force feedback-based sizing systems that supply information to the user on the actual force magnitude experienced by the sizing element. Such systems can be used in actual sizing procedures, or for analysis of different orifice characteristics to provide empirical information for use in calibrating the ball-detent clutch-based sizers described above.

Figure 15:
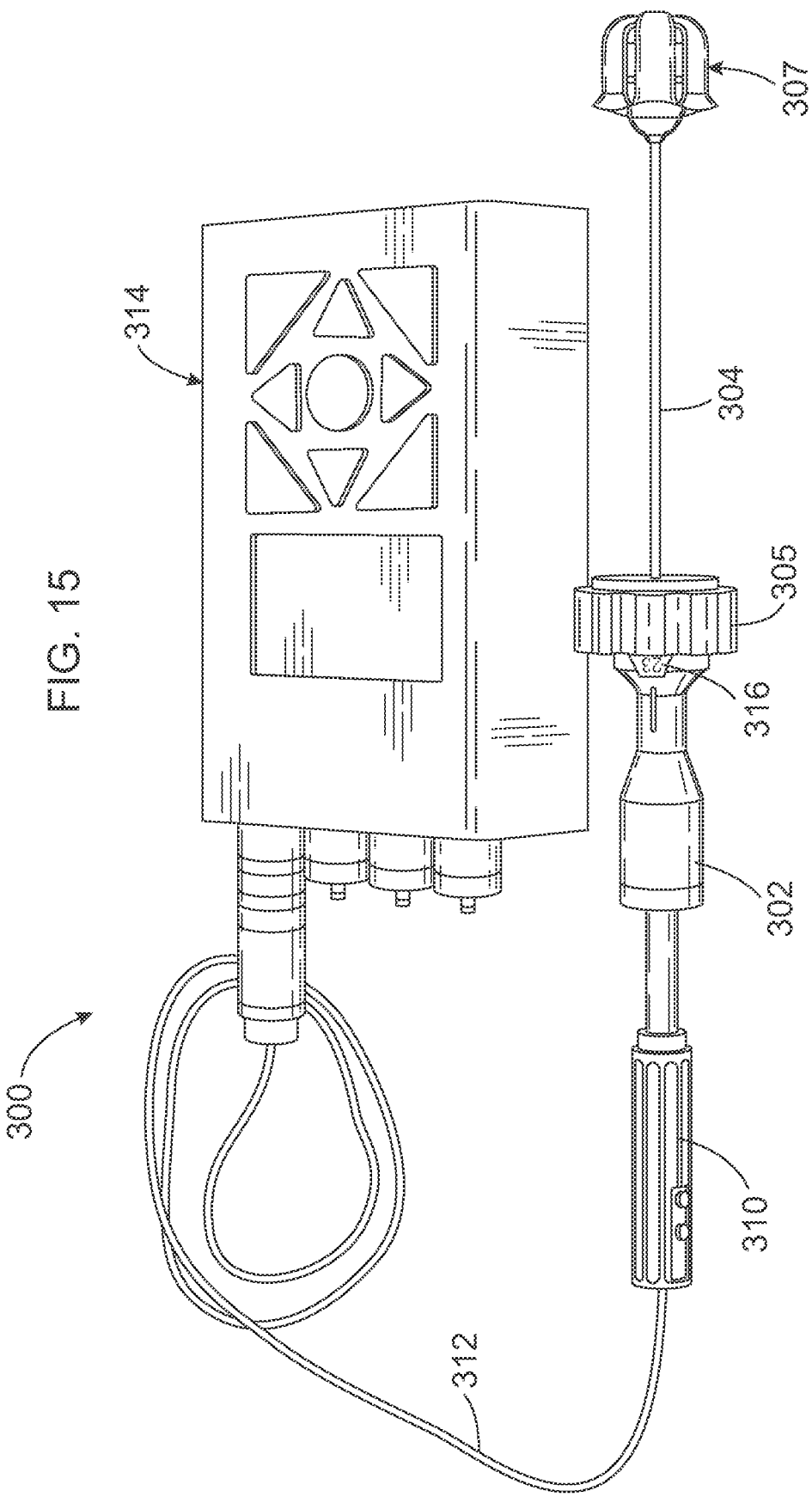
FIG. 15 is a schematic view of a feedback-based heart valve sizer that utilizes a torque sensor and display in conjunction with a sizing element to determine the valve orifice size.

For example, FIG. 15 shows a first embodiment of a force feedback-based sizing system 300 having a handle 302, a shaft 304, an actuator dial 305, and a sizing element 307 such as described above. A torque sensor 310 connected to a proximal end of the handle 302 is connected to sense the torque imparted to the actuator dial 305, for example, which expands the sizing element 307 against the surrounding orifice. The torque sensor 310 connects via a wire 312 to a display/data recording unit 314 to monitor and collect torque readings.

In use, the sizing element 307 is inserted into the annulus, orifice or structure whose diameter is being measured. While holding the torque sensor 310, the actuator dial 305 is rotated slowly until the next size increment is displayed in the window 316. The peak torque shown on the display/data recording unit 314 is then noted/recorded along with the diameter of the sizing element 307. The process is repeated for greater size increments. Ultimately, the torque data is converted to outward radial force or pressure data exerted by the sizing element 307 on the surrounding annulus. This information can be useful in calibrating a ball-detent clutch system as described above, such as by identifying the proper springs to use for a particular type of tissue or type of patient. More directly, the force feedback based sizer system 300 can be used to size a valve annulus, with the surgeon identifying the appropriate size not based on when the clutch slips but instead when a particular torque is reached. In that case, the clutch system may be set to have a relatively high torque threshold before it slips, though not too high to cause any tissue damage.

It should be noted that instead of the torque sensor 310 connected to sense the torque applied, a linear force sensor may be coupled to measure the tension in one or the other of the elements described previously for actuating the sizing elements. For example, in the embodiment of FIGS. 1-6 (e.g., FIG. 5B) the hollow shaft 104 is driven distally while the cable or rod 120 is place in tension between the handle 102 and the hub 117. A force sensor in the handle 102 could be attached to the proximal end of the cable 120 to measure the tension, which can be used to determine the level of the reaction force of the annulus against the petals 108. Sensing the force in the cable 120 would actually be a more direct method than sensing torque, though either method is suitable. For the purpose of definition of terms, both the torque sensor and linear force sensor methods will be termed force-feedback sensors.

Figure 16A:
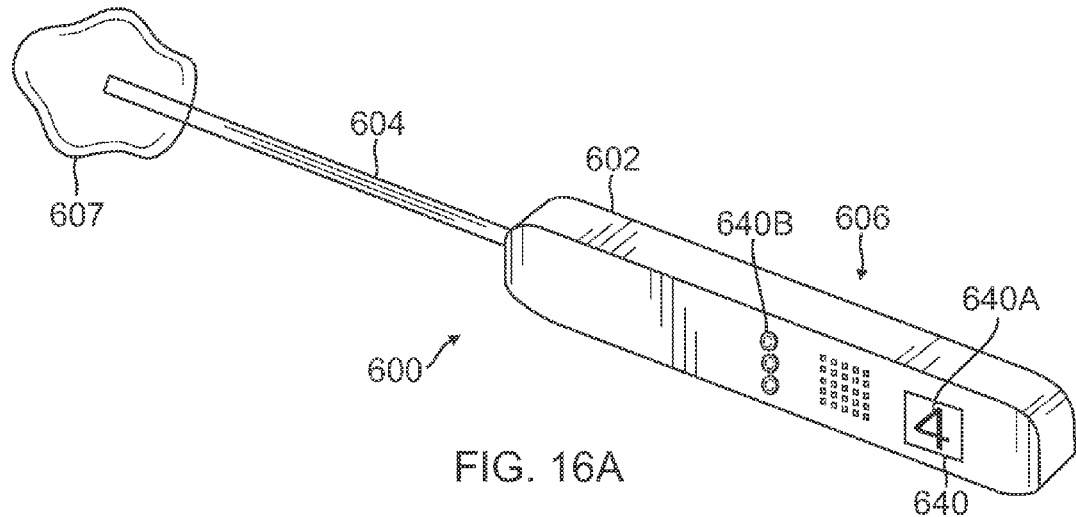
FIGS. 16A-16B show a force feedback-based heart valve sizer, according to another embodiment.

In another embodiment, a force feedback-based sizer 600 is provided. As shown in FIG. 16A, the sizer 600 has a hollow shaft 604 extending along the length of the sizer. A movable sizing element 607 is provided at the distal end of the shaft 604 and an actuation assembly 606 is provided at the proximal end of the shaft 604. The actuation assembly 606 includes an actuator 602 with a handle, and a force gauge disposed in the handle. The force gauge measures the force applied for operating the sizer.

The force gauge may provide a digital readout 640a of the force applied on a screen 640. In one embodiment, the force gauge may use varying colors (or colored lights) 640b to indicate if the applied pressure varies from a predetermined target range for the sizer. For example, if the force applied is within a predetermined target range the light may indicate green color. If the force applied is below the target range the color may be yellow, or red if the force applied is above the target range.

Figure 16B:
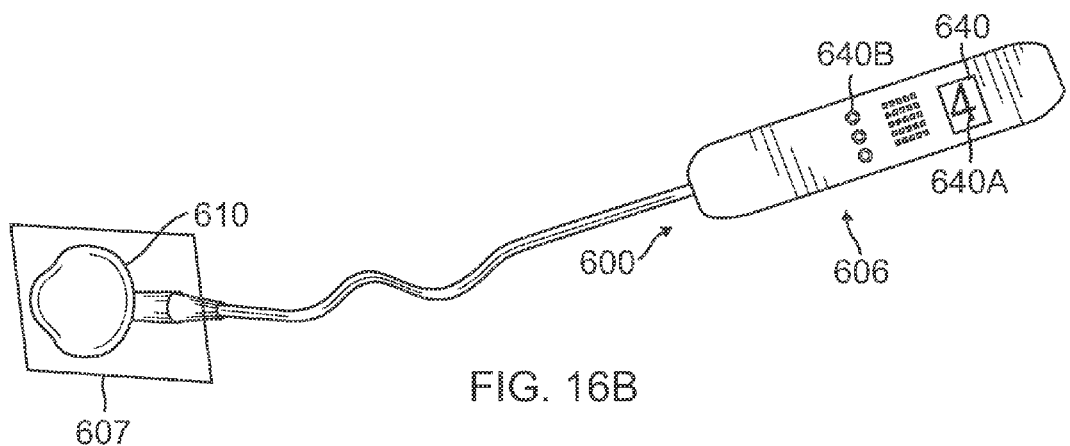

In one embodiment, as shown in FIG. 16B, the movable sizing element 607 includes a compliant spacer 610 that is filled with fluid and deforms with force. As force is applied, pressure within the spacer increases and is measured by a pressure gauge integrated into the handle.

FIGS. 17A and 17B show a heart valve sizer 700 where the electronic (light or digital readout) system of sizer 600 is replaced with a mechanical system. The system 700 features a malleable outer tube 703 with a flexible inner shaft 709 extending along the length of the sizer 700. The outer tube 703 is malleable and can be bent to any desired shape depending on the surgeon's preference and patient anatomy. The malleable outer tube 703 has a valve sizer 707 disposed at the distal end, and an actuation assembly 705 with a handle 702 disposed at its proximal end. A shaft marker (not shown) is attached to the shaft (not shown) that indicates an optimal force range of the force that may be applied to the heart valve sizer 700. A window 740 on the handle 702 of the actuator assembly 706 allows the surgeon to see the position of a marker attached to the shaft. Markings on the handle 702 indicate that the force level is optimal when aligned with the shaft marker (not shown). The spacer 707 is attached to a flexible inner shaft 709 which is inside the malleable outer tube 703. The flexible shaft 709 can move longitudinally within the outer tube 703 with minimal resistance. When in use, the sizer 700 is introduced between adjacent ribs in the patient. The surgeon then positions the spacer 707 in the valve annulus. The annulus exerts axial forces on the spacer 707. These axial forces from the spacer 707 are transmitted along the flexible inner shaft 705 to the spring system within the handle 702, and markings on the handle provide the feedback to the surgeon.

In yet another embodiment, as shown in FIGS. 18A and 18B, a sizer 800 is provided where the electronic (light or digital readout) system 600 is replaced with a mechanical system. The system 800 features a flexible outer helical coil 804 and malleable inner shaft 802 extending along the length of the system 800. The malleable inner shaft 802 can be bent to any desired shape depending on surgeon's preference and patient's anatomy. A valve sizer 807 is disposed at the distal end of the helical coil 804, while an actuation assembly 805 is disposed at the proximal end of the helical coil 804. A handle 801 operates the actuation assembly 805. A shaft marker (not shown) is attached to the shaft 802 that indicates an optimal force range of the force that may be applied to the heart valve sizer. A window 840 is provided which allows the user to see the position of a marker attached to the shaft. Markings on the handle 801 indicate that the force level is optimal when aligned with the shaft marker. The sizer 807 can slide over the malleable inner shaft 802 which is inside a flexible outer helical coil 804. The flexible outer helical coil 804 pushed by the spacer 807 can move longitudinally over the malleable inner shaft 802 with minimal resistance. When in use, the sizer 800 is introduced between adjacent ribs in the patient. The surgeon then positions the spacer 807 in the valve annulus. The annulus exerts axial forces on the spacer 807. These axial forces from the spacer 807 are transmitted along the flexible coil 804 to the spring system within the handle 801, and markings on the handle provide the feedback to the surgeon.

Figure 19C:
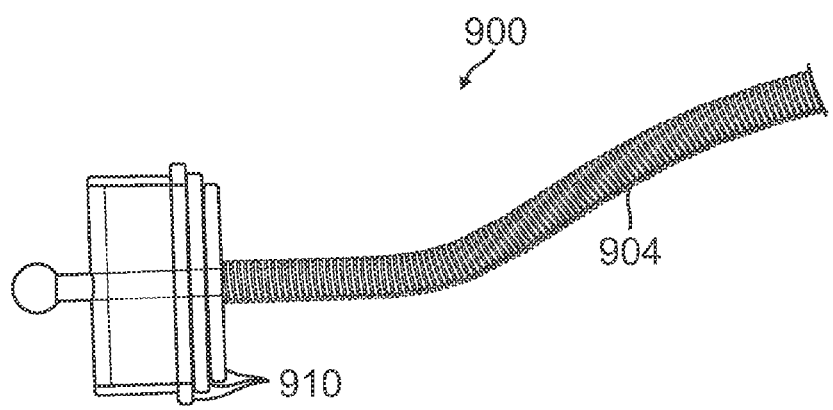
Figure 19D:
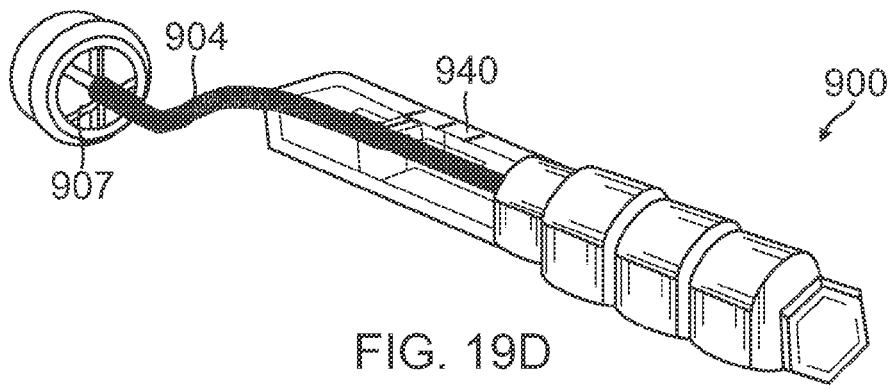
Figure 19E:
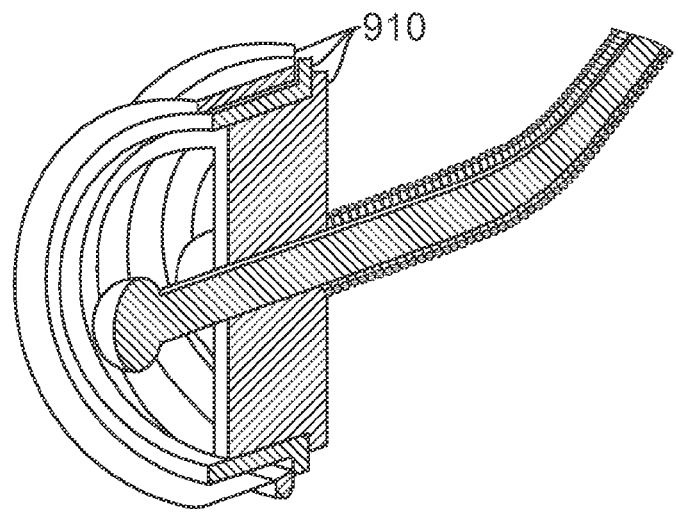

FIGS. 19A-19E show a heart valve sizer 900 with stackable hubs sliding over the same flexible outer helical coil and malleable inner shaft mechanism. The valve sizer 900 has a tube 904 extending along the length of the system. A valve sizer 907 is disposed at its distal end, while an actuation assembly 905 is disposed at the proximal end of the tube 904. The hubs 910 of varying diameters may be used to measure the annulus by stacking a next size hub onto existing smaller hubs. These hubs with incremental diameters mounted against the distal end of the outer spiral coil slide over a malleable inner shaft till an optimal fit is attained. If the sizer hub seems undersized when being pushed through the annulus, a bigger hub head can be moved down the tube 904 and attached to the initial hub either by a snapping connection or a luer-like quick connection. FIGS. 19B-19D show three hubs 910 stacked onto the distal end of the tube 904, while FIG. 19E shows a cross-sectional view of the distal end of the sizer 900 with three hubs 910 stacked on the coil 904.

Figure 20:
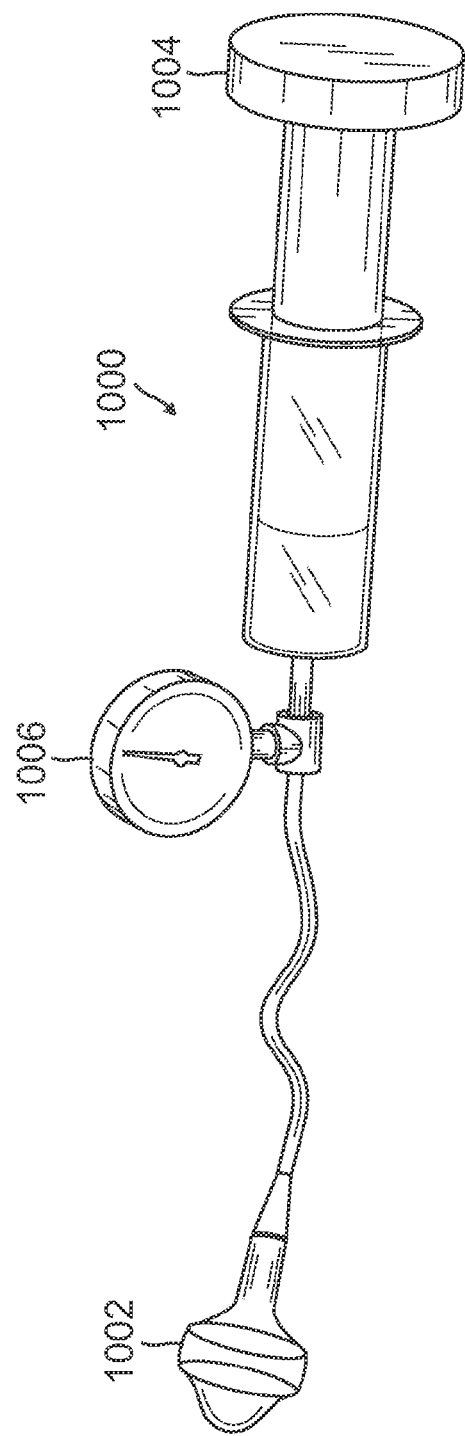
FIG. 20 shows a heart valve sizer with a pressure gauge.

FIG. 20 shows an alternate embodiment of a force-based heart valve sizer 1000 with a syringe 1004 and a pressure gauge 1006. The compliant hub 1002 is inflated with fluid pressurized by the syringe 1004. The pressure applied to the hub 1002 to size the valve annulus is measured by the pressure gauge 1006.

Figure 21:
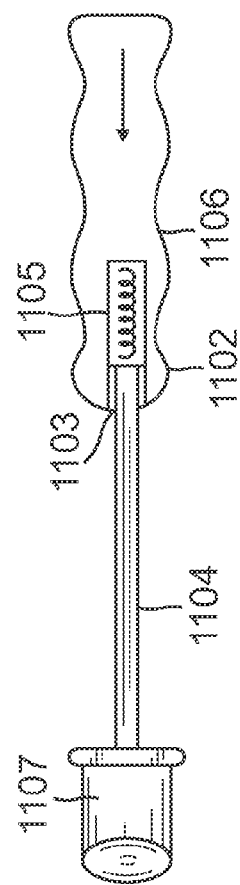
FIG. 21 shows a cross-sectional view of a force feedback-based heart valve sizer, according to yet another embodiment.

FIG. 21 shows a cross-sectional view of a force-based sizer 1100. The hub 1107 is attached to the distal end of the shaft 1104. The handle 1102 of the actuator assembly 1106 has an actuation mechanism comprising at least a spring 1105. As the hub 1107 moves towards the handle 1102, the shaft 1104 moves into the handle cavity 1103. Interfering features on the shaft 1104 and handle cavity 1103 eventually come into contact. As this interference is overcome, a tactile and/or audible 'click' is experienced. By adjusting the amount of interference, the device can be calibrated to a target force level. If no spring is present, then the device would provide minimal feedback to the operator until the interfering features came into contact. A spring 1105 that presents less force than the target force level would provide increasing tactile resistance to the operator as force was applied. Once actuated, the shaft 1104 would remain positioned proximally within the handle 1102. If a spring 1105 that is strong enough to overcome the target force level is used, then the device would return to its expanded length after the operator stops applying force to the device.

A force feedback-based heart valve sizer enables limiting, controlling and measuring axial forces at the sizer's distal end being inserted into the heart. The force feedback-based heart valve sizer enables sizing the heart valve annulus in a controlled manner, thereby limiting the maximum force applied and minimizing the risk of tissue damage.

The force feedback-based valve sizer disclosed here has several advantages over the currently used valve sizers. The first advantage is its adjustability, which allows a single sizer to cover the entire range of valve sizes. The use of a single one-size-fits-all sizer instead of multiple static sizers reduces clutter in the operating field and makes sizing the patient's annulus quicker, thereby potentially reducing bypass time during the procedure. Another advantage of the device over existing valve sizers is its ability to collapse radially. This feature has the potential to facilitate MIS surgical procedures which are performed through small surgical incisions. A static sizer may be too large to fit though an MIS incision, particularly if the procedure takes advantage of a collapsible MIS surgical valve. A further advantage of this device is the use of force-based sizing. The mechanism used to expand the sizer contains a ratchet mechanism that limits the amount of force the sizer applies to the annulus. The force limit can be set to achieve proper sizing of the annulus while eliminating the potential for over-expanding and damaging the annulus. This may be particularly important in MIS valve replacement procedures where visualization is poor and the surgeon may not be able to use their sense of "feel" to determine the proper annulus size.

Heart valve sizers, as well as other body cavity sizers, may be reduced in profile (diameter) to be used in minimally-invasive or percutaneous contexts. For instance, currently there is a great deal of ongoing work to develop systems for replacing heart valves percutaneously through a patient's vasculature without the need to stop the heart and place the patient on cardiopulmonary bypass. Currently, sizing for such procedures is done using fluoroscopy, which aside from exposing the patient and operating room staff to radiation is not as accurate as desirable. Accurate sizing of the heart valve annulus remains an issue, and the present application provides a clutch-based sizer in FIGS. 22-26 that may be used percutaneously.

FIGS. 22A-22C show a catheter-based sizing element 1200 in several stages of expansion. The sizing element 1200 includes a central hub 1202 that receives an actuation rod 1204 at a proximal end thereof. As will be shown, the actuation rod 1204 acts on a plurality of proximal levers 1206 that move outward in conjunction with a plurality of distal levers 1208 to radially displace axial sizing petals 1210. Because the lengths of the proximal and distal levers 1206, 1208 are the same, the sizing petals 1210 remain parallel to the hub 1202 axis while being displaced outward.

In a collapsed, delivery configuration, shown in FIG. 22A, the sizing element 1200 may have an outer diameter d of about 6 mm, sufficiently small to enable passage through an 18Fr percutaneous catheter (not shown) advanced through the femoral artery to one of the heart valve annulus, as is known. The profile of the sizing element 1200 could be further reduced to pass through even smaller catheters. A partially expanded sizing element 1200 in FIG. 22B has an outer diameter $D_1$ of about 19 mm, while a fully expanded sizing element 1200 in FIG. 22C has an outer diameter $D_2$ of about 29 mm. As with the various sizers discussed previously, the petals 1210 expand outward into contact with the valve annulus until a reaction force caused the clutched drive (not shown) to slip. As before, the clutch drive preferably has a size indicator (as with size indicators 133 on the clutch ring 121 in FIG. 3A) that displays the diameter of the sizing element 1200 at all times, such that when the clutch slips the user is aware of the valve annulus size, and thus the proper prosthetic heart valve size needed.

FIGS. 23 and 24A-24B are further views of the catheter-based sizing element 1200, and in particular FIG. 24B shows the outward movement of the connected levers 1206, 1208 and sizing petals 1210. Distal movement of the actuation rod 1204 acts on a plurality of small fingers 1212 on each proximal lever 1206 to cause the levers to pivot outward about pivot pins 1214 journaled in bores in the hub 1202, as seen in FIGS. 25 and 26. In this regard, the hub 1202 comprises a generally cylindrical body having a series of radially-projecting axial ribs 1216 between which each movable "segment" of the sizing element 1200 initially resides. Each movable segment includes one each of the levers 1206, 1208 and sizing petals 1210 connected together at hinges. Both the proximal and distal levers 1206, 1208 rotate about pins journaled in the sides of adjacent axial ribs 1216, and are each connected to rotate about opposite ends of a sizing petal 1210. Although not shown, the actuation rod 1204 desirably continues the length of the hub 1202 so that it can also act on similar fingers formed on the distal levers 1208, and thus produce an outward force on both levers.

The actuation rod 1204 could be driven by a clutch-based actuator, such as is shown above with respect to FIG. 2A-2C or 7A-7C. In particular, a ball-spring-detent mechanism that drives a lead screw is preferred as the sensitivity to environmental factors is relatively low.

If the sizing element 1200 is used in a beating heart procedure when the heart is pressurized, the force limit of the sizer will be set relatively low. The sizing element 1200 will essentially act as a touch probe and begin to slip when all of the petals (6 in the illustrated embodiment) contact the annulus with a minimum amount of force.

FIGS. 27 and 28 are schematic views of a balloon catheter inflation system 1300 that utilizes a clutch-limiter as described herein to limit the maximum inflation pressure. Inflation systems 1300 such as the illustrated embodiment are used for a variety of purposes, such as angioplasties, valvuloplasties, and for expanding arterial stents and more recently heart valves. The system 1300 includes a piston/cylinder chamber 1302 having a fluid outlet line 1304 that ultimately supplies pressurized saline or other inert fluid to a distal balloon 1306. In the illustrated embodiment, the balloon 1306 is being used to expand an anchoring frame of a hybrid-type of prosthetic heart valve which has a non-expandable valve portion as well; however the applications of the balloon inflation system 1300 should not be considered limited.

The actuator of the system 1300 includes a piston shaft 1310 that may be threaded within a bore in the piston/cylinder chamber 1302 so as to advance axially upon rotation of a clutch-limited actuator 1312. As the piston shaft 1310 advances, fluid is forced through the line 1304 to inflate the balloon 1306. A gauge 1314 displays the pressure within the fluid, and thus the pressure within the balloon 1306.

As seen in FIG. 28, the actuator 1312 preferably includes a series of springs 1316 that bias bearing 1318 outward into detents (not shown) formed on an inner surface of the handle of the actuator 1312. As with the embodiment of FIGS. 2A-2C, the springs 1316 and bearings 1318 are retained within an inner clutch member that is rigid with the shaft 1310. The actuator 1312 may be turned until the reaction torque from displacing the shaft 1310 exceeds a threshold value, at which point the bearings 1318 are forced inward against the springs 1316 and the clutch slips.

The system 1300 is a relatively simple, inexpensive solution to percutaneous inflation of heart valves and other devices. The clutch mechanism limits the maximum inflation pressure, which can be calibrated to induce a predetermined amount of device expansion. The system 1300 can be retrofitted to existing inflation devices, and acts as a safety feature to prevent over-inflation and possibly rupture of the balloon. There is a linear, predictable relationship between the amount of torque applied by the actuator 1312 and the fluid pressure generated by the advancing piston shaft 1310, and the relatively robust and precise action of the ball-spring-detent clutch makes limiting the pressure in the operating room environment highly repeatable and accurate.

The above description merely describes the preferred embodiments and it is understood that variations of the preferred embodiment are within the scope of the invention which is defined by the claims. For example, although it is preferred to use the valve sizers when performing a minimally invasive valve replacement procedure, the valve sizer may also be used in a conventional open-chest procedure.

I claim:

1. A method of sizing a patient's cardiac valve annulus, comprising:
providing a valve sizer having a shaft with a proximal end and a distal end and an expandable sizing element coupled to the distal end of the shaft, the sizing element being radially expandable between a first retracted position and a second expanded position, the valve sizer further having an actuator assembly comprising an actuator that moves relative to a handle, a clutch ring mounted at the proximal end of the shaft and coupled for rotation to the actuator via a clutch mechanism, and a stationary rod extending through at least a portion of the shaft, wherein the shaft is connected to the clutch ring so that movement of the actuator transmits through the clutch mechanism to the clutch ring and shaft and causes axial movement of the shaft, wherein the axial movement of the shaft causes radial expansion of the sizing element, wherein the actuator comprises an actuator ring and the sizing element includes a central hub, where the stationary rod is fixed with respect to both the handle and the central hub, and wherein the clutch ring is connected via a screw thread to the handle so that rotation of the clutch ring causes axial movement thereof and of the shaft;
inserting the valve sizer in the first retracted position into the patient so that the sizing element is positioned within the valve annulus; and
rotating the handle until the clutch mechanism of the actuator assembly begins to slip indicating that the sizer has applied a desired outward force to the annulus.

2. The method of claim 1, wherein the clutch mechanism comprises a plurality of bearings biased by springs into detents.

3. The method of claim 2, wherein the plurality of bearings and the springs are held within the clutch ring and the detents are formed on an inner surface of the actuator ring.

4. The method of claim 1, wherein the sizing element includes a plurality of sizing petals radially expandable between the first and second positions.

5. The method of claim 4, wherein the plurality of sizing petals move in a plane substantially perpendicular to a longitudinal axis defined by the shaft.

6. The method of claim 4, wherein the shaft moves axially and contacts and pivots a lever for each of the petals, wherein pivoting of the levers causes radial expansion of the petals.

7. The method of claim 4, wherein the shaft moves axially and connects to a camming member that directly contacts and causes radial expansion of the petals.

8. The method of claim 4, wherein the plurality of petals defines a cylindrical annulus portion and an outwardly-extending flange on a proximal end of the cylindrical annulus portion.

9. The method of claim 8, wherein the outwardly-extending flange has an axially undulating peripheral shape.

10. A method of sizing a patient's anatomical orifice, comprising:
providing a valve sizer having:
a proximal handle having an actuator;
a shaft extending distally from the handle;
a surgical sizing element coupled to a distal end of the shaft, the sizing element having a radially variable size controlled by movement of at least a portion of the shaft; and
a clutch mechanism in the proximal handle configured to transmit movement from the actuator to the portion of the shaft that controls the size of the sizing element, wherein the sizing element and clutch mechanism are coupled together such that outward radial expansion of the sizing element into contact with a surrounding orifice transmits via the shaft a reaction force back to the clutch mechanism which slips at a predetermined reaction force corresponding to a desired outward force applied by the sizing element to the orifice and halts further outward radial expansion of the sizing element, wherein the shaft comprises a rod extending through a hollow shaft and the actuator comprises an actuator ring, where the rod is fixed with respect to both the handle and a central hub of the sizing element, and wherein rotation of the actuator ring causes axial movement thereof and of the hollow shaft until the clutch mechanism slips;
inserting the valve sizer into the patient so that the sizing element is positioned within the orifice; and
manipulating the actuator until the clutch mechanism begins to slip indicating that the sizer has engaged the orifice to a predetermined level.

11. The method of claim 10, wherein the orifice is a cardiac valve annulus, and the proximal handle includes a plurality of orifice sizes indicators and a display that stops on one of the indicated sizes when the clutch slips.

12. The method of claim 10, wherein the clutch mechanism further comprises a clutch ring mounted at the proximal end of the shaft and coupled for rotation to the actuator ring via a clutch mechanism and a plurality of bearings and springs held within the clutch ring, the plurality of bearings being biased by the springs into detents formed on an inner surface of the actuator ring.

13. The method of claim 10, wherein the sizing element is radially expandable between a retracted first position and an expanded second position, and wherein the sizing element includes a plurality of sizing petals radially expandable between the first and second positions.

14. A method of sizing a patient's anatomical orifice, comprising:
   providing a valve sizer having:
      a proximal handle having an actuator;
      a shaft extending distally from the handle;
      a surgical sizing element coupled to a distal end of the shaft, the sizing element having a radially variable size controlled by movement of at least a portion of the shaft;
      a clutch mechanism in the proximal handle configured to transmit movement from the actuator to the portion of the shaft that controls the size of the sizing element, wherein the sizing element and clutch mechanism are coupled together such that outward radial expansion of the sizing element into contact with a surrounding orifice transmits via the shaft a reaction force back to the clutch mechanism which slips at a predetermined reaction force; and
      a sensor which senses a reaction force on the sizing element caused by outward radial expansion of the sizing element into contact with a surrounding orifice, wherein the shaft comprises a rod extending through a hollow shaft, the rod being fixed with respect to both the handle and a central hub of the sizing element, wherein axial movement of the hollow shaft with respect to the rod expands the sizing element, and wherein manipulation of the actuator causes axial movement of the hollow shaft and the sensor is a linear force sensor coupled to measure tension or compression in either the rod or the hollow shaft;
   inserting the valve sizer into the patient so that the sizing element is positioned within the orifice; and
   manipulating the actuator to expand the sizing element until the sensor senses a desired reaction force less than the predetermined reaction force and halting expansion of the sizing element when the desired reaction force is sensed.

15. The method of claim 14, wherein the orifice is a cardiac valve annulus, and the proximal handle includes a plurality of orifice sizes indicators and a display that stops on one of the indicated sizes when the desired reaction force is sensed.

16. The method of claim 14, wherein the actuator comprises an actuator ring, the valve sizer further having a clutch ring mounted at the proximal end of the shaft and coupled for rotation to the actuator via the clutch mechanism, and wherein the clutch mechanism comprises a plurality of bearings biased by springs into detents, and the plurality of bearings and the springs are held within the clutch ring and the detents are formed on an inner surface of the actuator ring.

17. The method of claim 14, wherein the sizer is configured for percutaneous delivery through a catheter and the sizing element in a first retracted position has a diameter small enough to enable passage through the catheter, and wherein the method includes passing the sizing element and shaft through a catheter.

* * * * *